(12) United States Patent
Sadakane et al.

(10) Patent No.: US 9,119,575 B2
(45) Date of Patent: Sep. 1, 2015

(54) PANORAMIC TOMOGRAPHY X-RAY APPARATUS AND IMAGE PROCESSING DEVICE

(71) Applicant: J. Morita Manufacturing Corporation, Kyoto-shi, Kyoto (JP)

(72) Inventors: Tomoyuki Sadakane, Kyoto (JP); Hodaka Ishii, Kyoto (JP)

(73) Assignee: J. MORITA MANUFACTURING CORPORATION, Kyoto (JP)

( * ) Notice: Subject to any disclaimer, the term of this patent is extended or adjusted under 35 U.S.C. 154(b) by 126 days.

(21) Appl. No.: 13/665,758

(22) Filed: Oct. 31, 2012

(65) Prior Publication Data

US 2013/0108011 A1    May 2, 2013

(30) Foreign Application Priority Data

Nov. 2, 2011    (JP) ................................. 2011-241360
Oct. 26, 2012   (JP) ................................. 2012-237002

(51) Int. Cl.

| *A61B 6/03* | (2006.01) |
|---|---|
| *A61B 8/13* | (2006.01) |
| *G06T 1/00* | (2006.01) |
| *G01T 7/00* | (2006.01) |
| *A61B 6/14* | (2006.01) |

(52) U.S. Cl.
CPC ... *A61B 6/14* (2013.01); *A61B 6/03* (2013.01); *G06T 2207/10081* (2013.01); *G06T 2207/30036* (2013.01)

(58) Field of Classification Search
CPC .. A61B 6/03; A61B 6/14; G06T 2207/30036; G06T 2207/10081

USPC .......................................................... 378/39
See application file for complete search history.

(56) References Cited

U.S. PATENT DOCUMENTS

| 4,907,251 A | 3/1990 | Mork et al. |
|---|---|---|
| 2010/0067650 A1 | 3/2010 | Arai et al. |
| 2010/0074403 A1* | 3/2010 | Inglese et al. .................. 378/39 |

FOREIGN PATENT DOCUMENTS

| EP | 2156792 A | 2/2010 |
|---|---|---|
| JP | H02-140150 A | 5/1990 |
| JP | 4-144549 | 5/1992 |
| JP | 8-215192 | 8/1996 |
| JP | 2003-245277 A | 9/2003 |
| JP | P2004-313576 A | 11/2004 |
| JP | P2008-86659 A | 4/2008 |
| JP | 2008-229322 A | 10/2008 |
| JP | 2009-131656 A | 6/2009 |
| JP | P2010-46486 A | 3/2010 |
| JP | P2011-83499 A | 4/2011 |

\* cited by examiner

*Primary Examiner* — Glen Kao
*Assistant Examiner* — Dani Fox
(74) *Attorney, Agent, or Firm* — DLA Piper LLP (US)

(57) ABSTRACT

A panoramic tomography X-ray apparatus including an image information processing part, a display part, and a position setting part. The image information processing part retrieves a frame image information from a storage part and superimposes overlapped portions of images along a tomographic plane corresponding to a dental arch to generate a panoramic tomographic image. The display part displays the panoramic tomographic image generated by the image information processing part. The position setting part sets, in a median portion including a median line of an object, the position of the tomographic plane regarding depth direction of the object.

23 Claims, 18 Drawing Sheets

F I G. 1
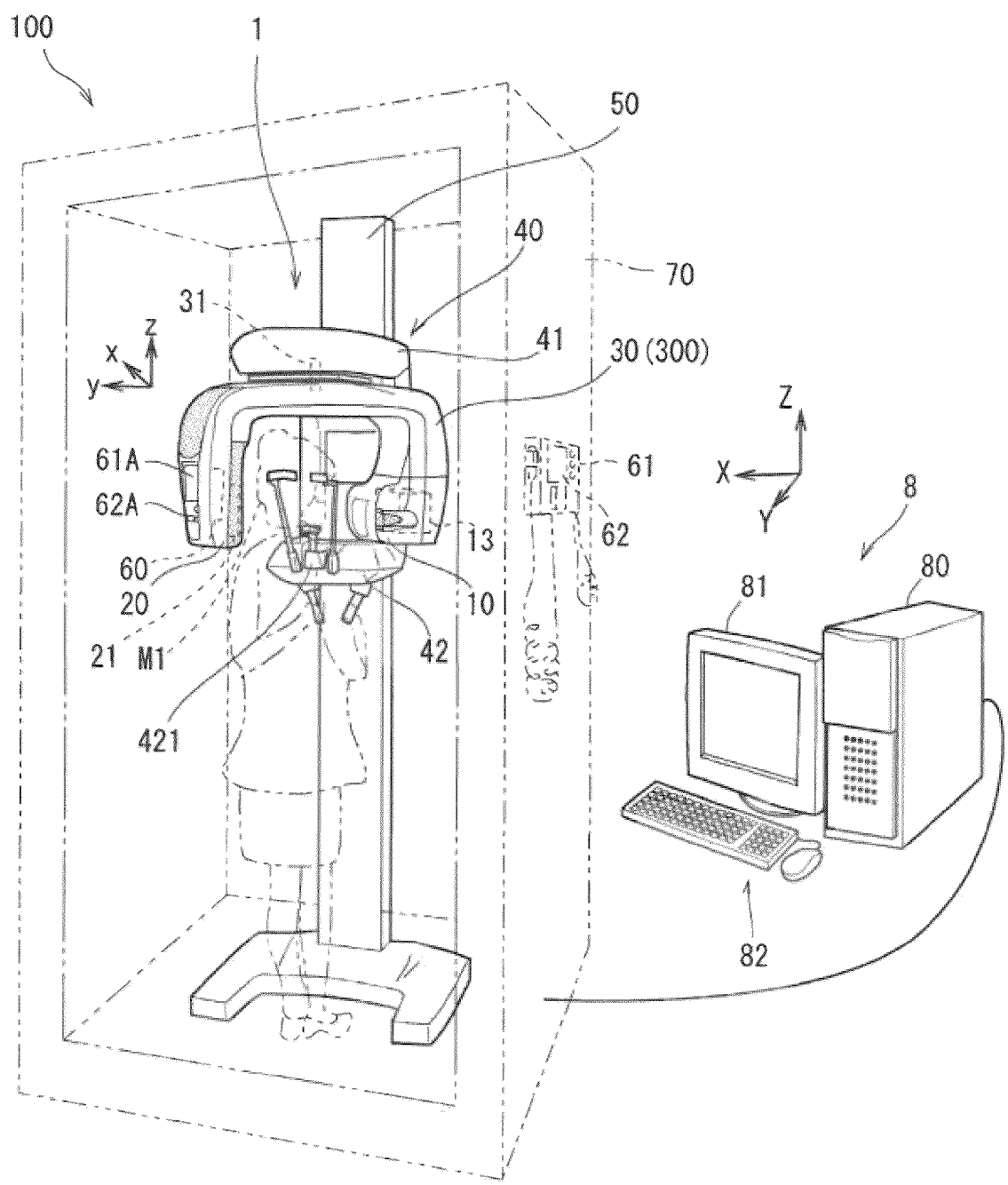

F I G. 2
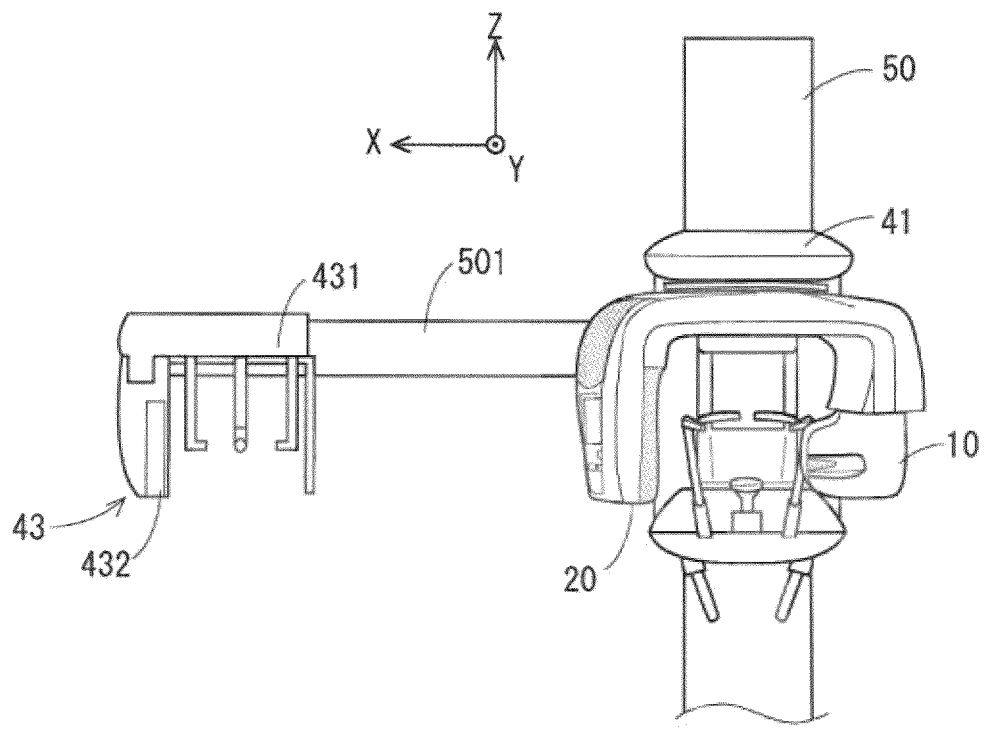

F I G. 4
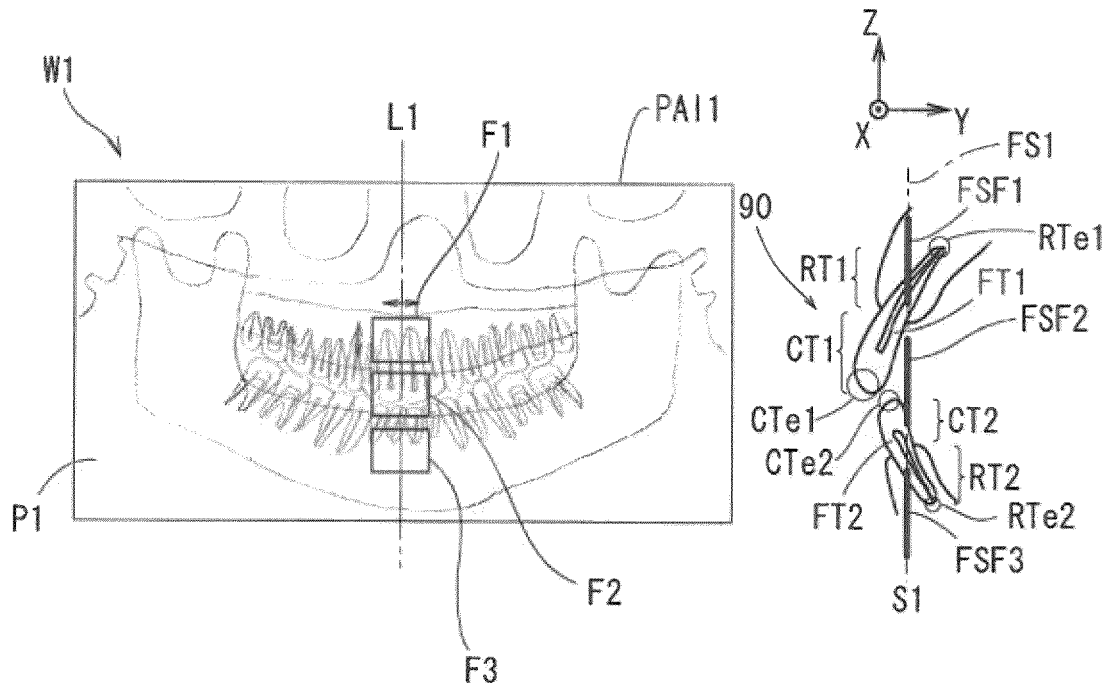
F I G. 5
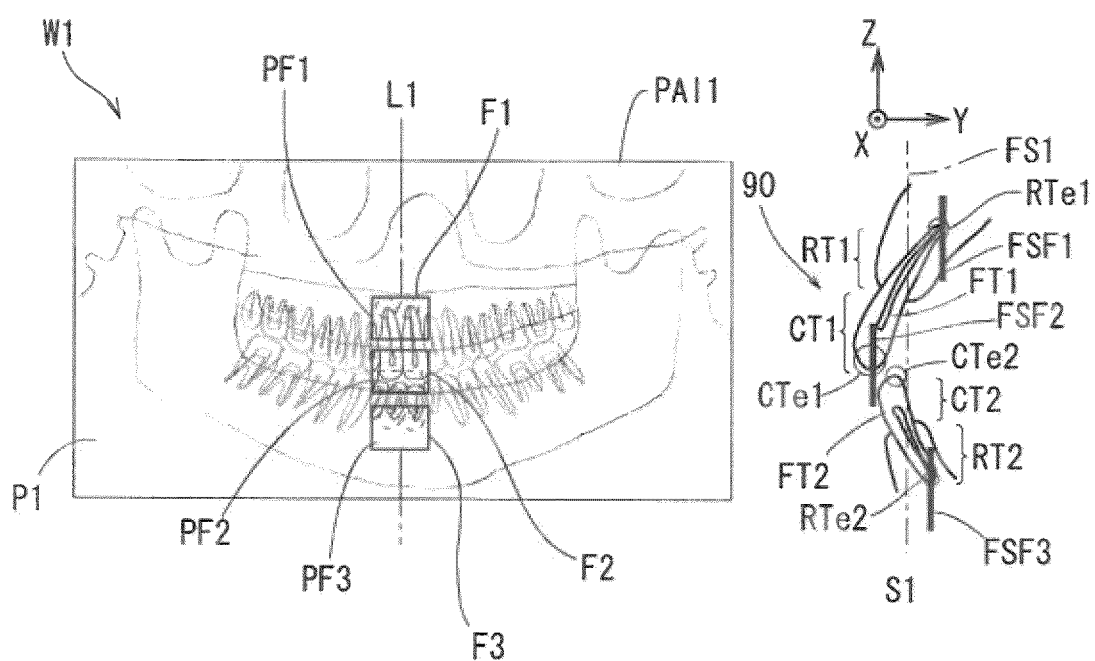

F I G . 6
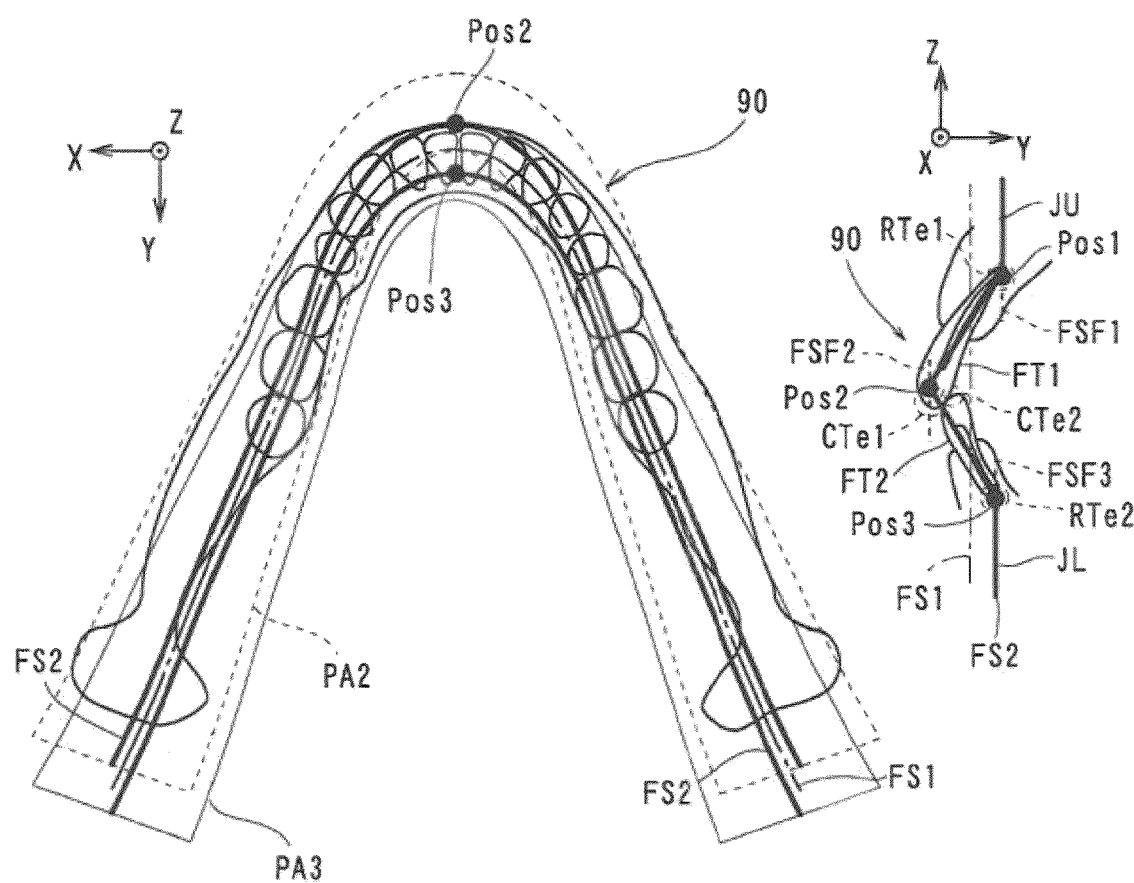

F I G . 1 1
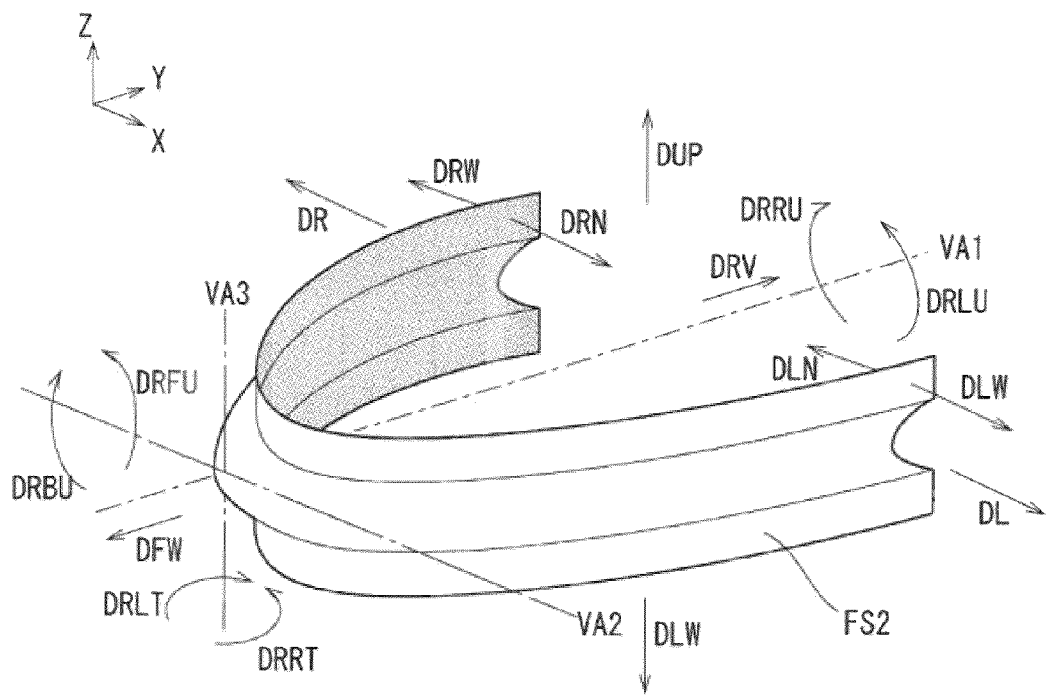

F I G . 1 3 A
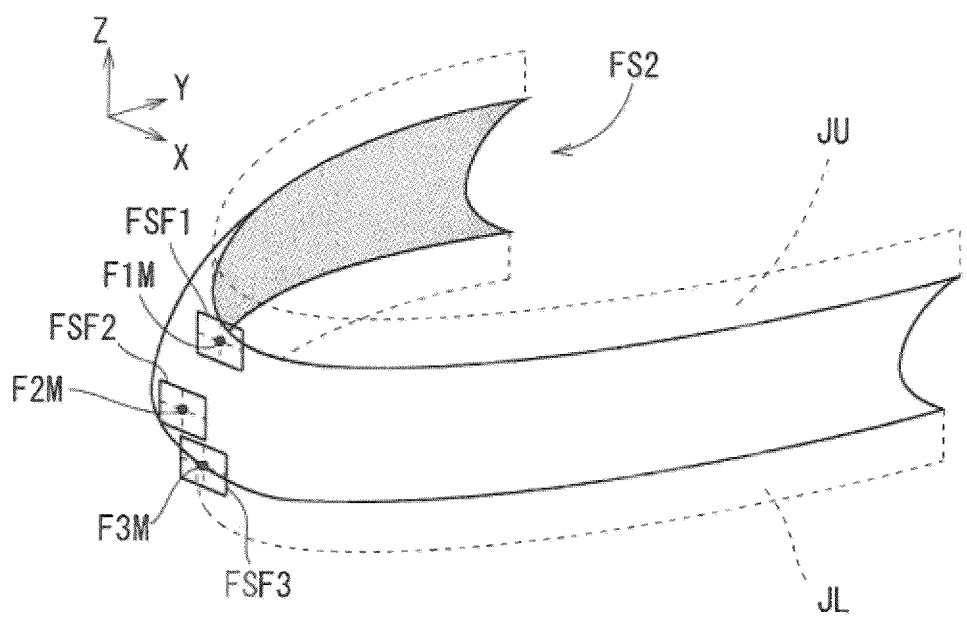

F I G. 1 4 A
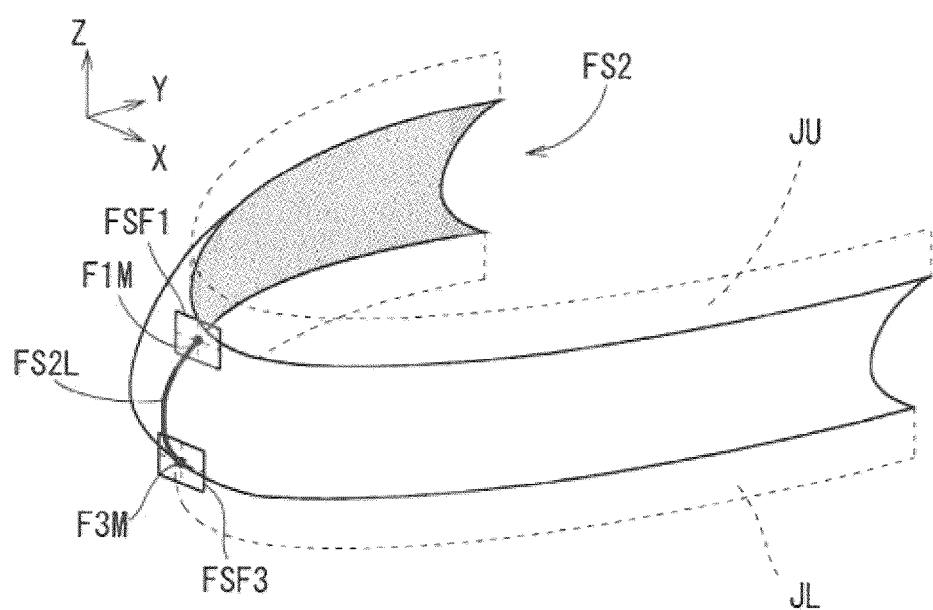

PANORAMIC TOMOGRAPHY X-RAY APPARATUS AND IMAGE PROCESSING DEVICE

BACKGROUND OF THE INVENTION

1. Field of the Invention

The present invention relates to a technology of generating panoramic tomography X-ray images.

2. Description of the Background Art

In dental treatment, panoramic X-ray tomography is performed for checking the conditions of the teeth (dentition) and gums of patients. In this panoramic X-ray tomography, an X-ray source and an X-ray detector are caused to revolve about an object (patient) in the state of facing each other so as to sandwich a jaw portion of the object therebetween, to thereby collect pieces of X-ray transparent data (frame images) at a predetermined frame rate. Then, the computation process (shift addition) in which overlapped portions of images are superimposed along a tomographic plane corresponding to the shape of a dentition is performed, to thereby generate a panoramic tomographic image.

In order to generate a panoramic tomographic image with little blurring, it is desired to make a position of a tomographic plane correspond to the shape of the dentition as much as possible. Therefore, in Japanese Patent Application Laid-Open No. 2008-229322, the position of the dentition is specified from the image data obtained through X-ray CT tomography, and the panoramic tomographic plane is set at that position, to thereby obtain a panoramic tomographic image.

The panoramic X-ray tomography of Japanese Patent Application Laid-Open No. 2008-229322 can handle the shape of a dental arch peculiar to a patient. However, when CT imaging is performed, every portion other than the dental arch needs to be continuously irradiated with X-rays. Accordingly, from the viewpoint of the purpose to obtain a panoramic tomographic image, portions other than required need X-ray irradiation, leading to an excessive X-ray exposure.

Normally, the front teeth each extends while being inclined obliquely forward in the vicinity of the median line of the upper and lower jaws. It is, therefore, desirable to set a tomographic plane in accordance with the above-mentioned shape of the dentition, but in Japanese Patent Application Laid-Open No. 2008-229322 there is no particular description of the configuration for handling this shape.

SUMMARY OF THE INVENTION

The present invention is directed to a panoramic tomography X-ray apparatus.

A panoramic tomography X-ray apparatus according to a first aspect of the present invention includes: an X-ray generator for emitting X-rays; an X-ray detector including a plurality of detection elements outputting signals corresponding to the intensity of the X-rays to be incident thereon; a revolution mechanism for causing the X-ray generator and the X-ray detector to be opposed to each other with an object including a dentition sandwiched therebetween, and allowing the X-ray generator and the X-ray detector to revolve about the object; a storage part for successively accumulating and storing the signals output from the X-ray detector as image information when the X-ray generator revolving through the revolution mechanism emits the X-rays; an image information processing part for retrieving the image information from the storage part and superimposing overlapped portions of images along a tomographic plane corresponding to a dental arch to generate a panoramic tomographic image; a display part for displaying the panoramic tomographic image generated by the image information processing part; and a position setting part for setting, in a median portion including a median line of the object, a position of the tomographic plane regarding a depth direction of the object with the use of at least one image for position setting formed of a median-portion X-ray image including the median portion.

According to the panoramic tomography X-ray apparatus of the first aspect of the present invention, a panoramic tomographic image can be generated for a tomographic plane corresponding to the shape of dentition in the vicinity of the front teeth located in the median portion, with a small amount of X-ray exposure. As a result, a clear panoramic tomographic image of the dentition with little blurring can be obtained.

In a second aspect of the present invention, the panoramic tomography X-ray apparatus according to the first aspect further includes an operation part for receiving an input of the operation by an operator, wherein the position setting part causes the display part to display, as an image for position designation that forms the at least one image for position setting, the panoramic tomographic image regarding the dentition, and on the at least one image for position setting, the position setting part receives the designation of the position regarding the depth direction of the tomographic plane in the median portion via the operation part and allows a display of a tomographic image of the tomographic plane passing through the designated position received, as an X-ray image of the median portion, on the at least one image for position setting in a superimposed manner.

According to the panoramic tomography X-ray apparatus of the second aspect, therefore, a panoramic tomographic image is displayed as an image for position designation, and a new position of a tomographic plane is set, so that a panoramic tomographic image regarding the tomographic plane at the new position is displayed on the image for position designation in a superimposed manner. This makes it easier to set an optimum position of a tomographic plane.

In a third aspect of the present invention, in the panoramic tomography X-ray apparatus according to the second aspect, the position setting part allows a display of, for at least one partial area including at least the median portion, the panoramic tomographic image of the tomographic plane passing through the designated position as the median-portion X-ray image on the at least one image for position setting in a superimposed manner.

According to the panoramic tomography X-ray apparatus of the third aspect, a panoramic tomographic image is generated only for a partial area that is a part of the image for position designation. Therefore, the amount of computation process required for image generation can be reduced more compared with the case of generating a new panoramic tomographic image having the same size as that of the image for position designation.

In a fourth aspect of the present invention, in the panoramic tomography X-ray apparatus according to the third aspect, the position of the at least one partial area is changeable in a direction orthogonal to the depth direction by the input of the operation via the operation part on the panoramic tomographic image.

According to the panoramic tomography X-ray apparatus of the fourth aspect, therefore, the position of the partial area can be moved in a direction orthogonal to the depth direction, which enables to appropriately select the location at which the position in the depth direction is set in the median portion.

In a fifth aspect of the present invention, in the panoramic tomography X-ray apparatus according to any one of the second to fourth aspects, the position setting part receives the position regarding the depth direction for an upper jaw or a lower jaw in the median portion.

According to the panoramic tomography X-ray apparatus of the fifth aspect, therefore, the position in the depth direction of the tomographic plane can be set in the area of an upper jaw or a lower jaw.

In a sixth aspect of the present invention, in the panoramic tomography X-ray apparatus according to any one of the second to fifth aspects, the position setting part receives the designation of the position regarding the depth direction for an area that includes a tooth root portion of at least one tooth located in the median portion.

According to the panoramic tomography X-ray apparatus of the sixth aspect, therefore, the position in the depth direction of the tomographic plane can be set in the area of the tooth root portion.

In a seventh aspect of the present invention, in the panoramic tomography X-ray apparatus of any one of the second to sixth aspects, the position setting part receives the designation of the position regarding the depth direction for two areas including the tooth root portion of the at least one tooth located in the median portion and a tooth crown portion of the at least one tooth.

According to the panoramic tomography X-ray apparatus of the seventh aspect, therefore, the position in the depth direction of the tomographic plane can be set in both areas of the tooth root portion and the tooth crown portion.

In an eighth aspect of the present invention, in the panoramic tomography X-ray apparatus of any one of the second to seventh aspects, the position setting part receives the designation of the position regarding the depth direction for three areas including the tooth root portion of the at least one tooth of the upper jaw, the tooth root portion of the at least one tooth of the lower jaw, and occlusion portions of these teeth.

According to the panoramic tomography X-ray apparatus of the eighth aspect, therefore, the position in the depth direction of the tomographic planes can be set in three areas including the tooth root portion of the teeth of the upper jaw, the tooth root portion of the teeth of the lower jaw, and an occlusion portion of the teeth. This enables to set a tomographic plane corresponding to a shape of a dentition with high accuracy.

In a ninth aspect of the present invention, in the panoramic tomography X-ray apparatus according to any one of the first to eighth aspects, the position setting part sets the position of the tomographic plane such that the position of the tomographic plane changes along the median line in a non-linear manner in the depth direction.

According to the panoramic tomography X-ray apparatus of the ninth aspect, therefore, to a tomographic plane having a non-linear shape along the median line can be set.

In a tenth aspect of the present invention, in the panoramic tomography X-ray apparatus according to any one of the first to ninth aspects, the position setting part sets the position of the tomographic plane such that the position of the tomographic plane changes along the median line into a beak shape in the depth direction.

According to the panoramic tomography X-ray apparatus of the tenth aspect, therefore, a tomographic plane that deforms into a beak shape can be set so as to correspond to the shape of the portion in the vicinity of the front teeth of the upper jaw and the lower jaw.

In an eleventh aspect of the present invention, in the panoramic tomography X-ray apparatus according to any one of the first to tenth aspects, the tomographic plane has a curved plane along the dental arch.

According to the panoramic tomography X-ray apparatus of the eleventh aspect, therefore, the tomographic plane has a curved plane along the dental arch, which enables to generate a panoramic tomographic image of the entire dentition.

In a twelfth aspect of the present invention, the panoramic tomography X-ray apparatus according to any one of the first to eleventh aspects further includes a position detection part that detects a position of the object, and an adjustment part that adjusts the positional relationship among the object, the X-ray generator, and the X-ray detector based on the detection results by the position setting part.

According to the panoramic tomography X-ray apparatus of the twelfth aspect, therefore, panoramic X-ray tomography can be performed by appropriately adjusting the positional relationship among the X-ray generator, the X-ray detector, and the object.

The present invention is also directed to an image processing device used in the panoramic tomography X-ray apparatus described above.

An image processing device according to a thirteenth aspect of the present invention includes: a storage part for storing, when an X-ray generator emits X-rays while the X-ray generator and an X-ray detector are caused to revolve about an object in a state of being opposed to each other with the object sandwiched therebetween, signals output from the X-ray detector in accordance with the intensity of the X-rays as image information when the X-ray generator being revolved by the revolution mechanism emits the X-rays; an image information processing part for retrieving the image information from the storage part and superimposing overlapped portions of images along a tomographic plane corresponding to a dental arch to generate a panoramic tomographic image; a display part for displaying the panoramic tomographic image generated by the image information processing part; and a position setting part for setting, in a median portion including a median line of the object, a position of the tomographic plane regarding a depth direction of the object, with the use of at least one image for position setting formed of a median-portion X-ray images including the median portion.

In a fourteenth aspect of the present invention, the image processing device according to the thirteenth aspect further includes an operation part for receiving an input of operation by an operator, wherein the position setting part causes the display part to display, as an image for position designation that forms the at least one image for position setting, the panoramic tomographic image regarding the dentition, and on the at least one image for position setting, the position setting part receives the designation of a position regarding the depth direction of the tomographic plane in the median portion via the operation part and displays a tomographic image of the tomographic plane passing through the designated position received on the at least one image for position setting in a superimposed manner.

As seen from the above, the present invention has an object to provide a technology of generating a clear panoramic tomographic image by performing panoramic X-ray tomography with a small amount of X-ray exposure and appropriately setting a position of a tomography plane.

The above-described and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic perspective view showing a panoramic tomography X-ray apparatus according to a first preferred embodiment of the present invention;

FIG. 2 is a front view of a cephalostat applicable to the panoramic tomography X-ray apparatus;

FIG. 4 is a view showing a display screen for position setting of a tomographic plane;

FIG. 5 is a view showing the display screen when positions in a depth direction of partial tomographic planes are changed;

FIG. 6 is a schematic plan view showing a dentition of a lower jaw of an object;

FIG. 11 is an exemplary illustration for explaining the displacement adjustment or shape adjustment of the tomographic plane;

FIG. 13A is a view showing an example of setting a position of a tomographic plane FS2 with the use of partial tomographic planes FSF1 to FSF3;

FIG. 14A is a view showing an example of setting the position of the tomographic plane FS2 with the use of the partial tomographic planes FSF1 and FSF3;

DESCRIPTION OF THE PREFERRED EMBODIMENT

Description of the Preferred Embodiment

Figure 3:
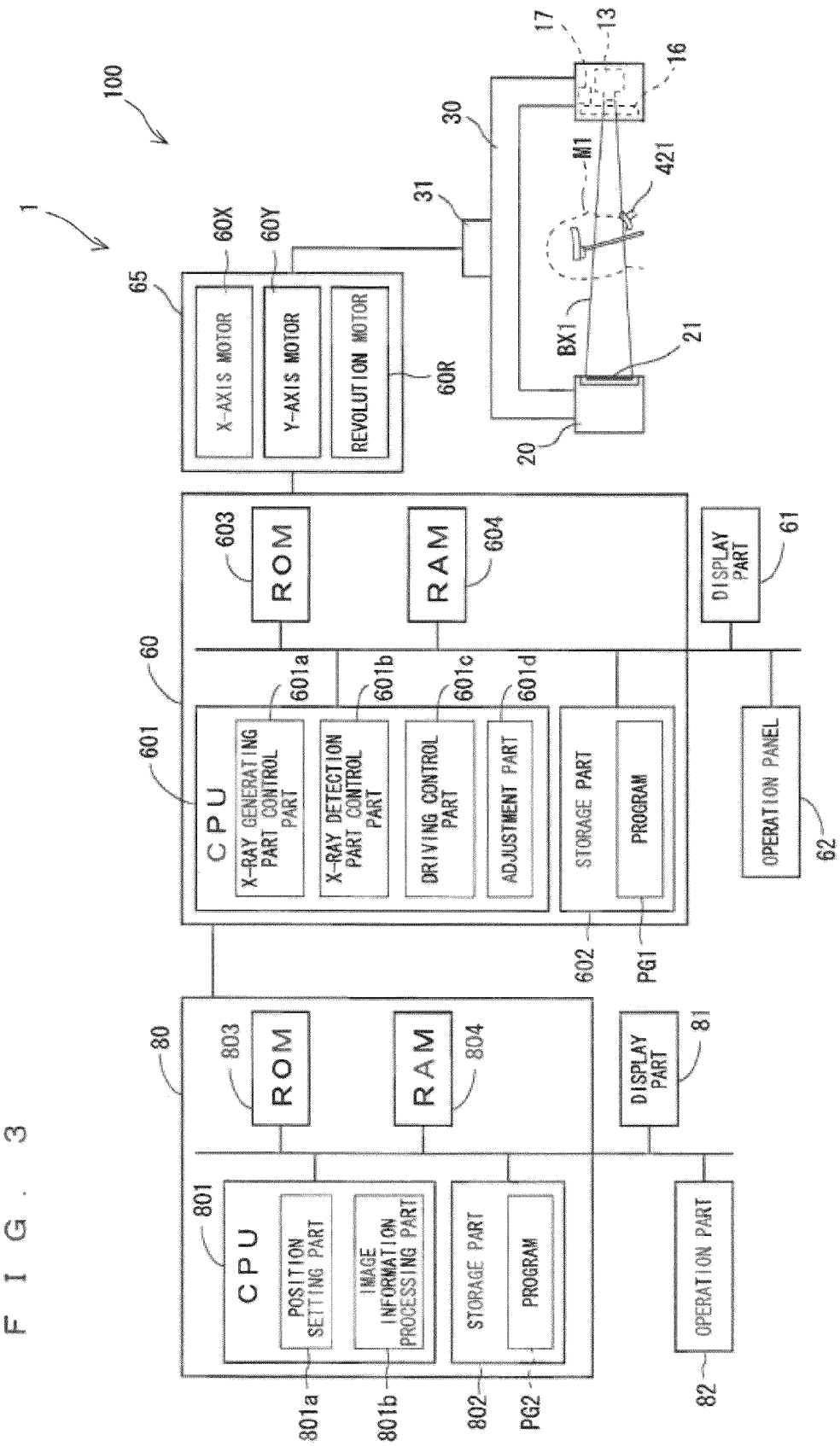
FIG. 3 is a block diagram showing the configuration of the panoramic tomography X-ray apparatus.

Hereinafter, a preferred embodiment of the present invention will be described in detail with reference to the accompanying drawings. It should be noted that any components described in the preferred embodiment are merely illustrative and should not be construed as limiting the scope of the present invention.

1. First Preferred Embodiment

<1.1 Configuration and Function of Panoramic Tomography X-Ray Apparatus>

FIG. 1 is a schematic perspective view showing a panoramic tomography X-ray apparatus 100 according to a first preferred embodiment of the present invention. The panoramic tomography X-ray apparatus 100 is roughly divided into two components: a main body unit 1 that performs X-ray imaging and collects pieces of projection data and an information processing device 8 that processes the pieces of projection data collected in the main body unit 1 and generates various images. The panoramic tomography X-ray apparatus 100 is configured so as to perform not only panoramic X-ray tomography but also normal X-ray computed tomography (CT).

The main body unit 1 includes an X-ray generating part 10, an X-ray detection part 20, a support part 300 (revolution arm 30), an elevator part 40, a support column 50, and a main-body control part 60. The X-ray generating part 10 emits an X-ray cone beam BX1 (see FIG. 3) having an X-ray flux toward an object M1. The X-ray detection part 20 detects X-rays emitted from the X-ray generating part 10. The X-ray generating part 10 and the X-ray detection part 20 are provided on the support part 300. The elevator part 40 holds the support part 300 in a suspended manner and is capable of moving up and down in the vertical direction on the support column 50. The support column 50 extends in the vertical direction.

An XYZ orthogonal coordinate system and an xyz orthogonal coordinate system are provided as required in, for example, FIG. 1. Herein, the direction (herein, vertical direction) parallel to the axial direction of a revolution shaft 31 is referred to as a "Z-axis direction", a direction intersecting the Z-axis direction is referred to as an "X-axis direction", and a direction intersecting the X-axis direction and the Z-axis direction is referred to as a "Y-axis direction". The X-axis and Y-axis directions may be set appropriately. Herein, the right-and-left direction of a subject, which is the object M1, when the subject is positioned in the panoramic tomography X-ray apparatus 100 to face the support column 50 is defined as the X-axis direction, wherein the front-and-back direction of the subject is defined as the Y-axis direction. The X-axis direction, the Y-axis direction, and the Z-axis direction are assumed to be orthogonal to each other in this preferred embodiment. In some cases, hereinafter, the Z-axis direction is referred to as the vertical direction, and the direction on a plane two-dimensionally defined by the X-axis direction and the Y-axis direction is referred to as the horizontal direction.

The xyz orthogonal coordinate system is a three-dimensional coordinate system defined on the revolution arm 30 that revolves. Herein, the direction in which the X-ray generating part 10 and the X-ray detection part 20 are opposed to each other is referred to as a "y-axis direction", a horizontal direction orthogonal to the y-axis direction is referred to as an "x-axis direction", and a vertical direction orthogonal to the x-axis and y-axis directions is referred to as a "z-axis direction". In this preferred embodiment, the Z-axis direction is the same as the z-axis direction. The revolution arm 30 in this preferred embodiment rotates about the revolution shaft 31 extending in the vertical direction. Accordingly, the xyz orthogonal coordinate system rotates about the Z-axis (=z-axis) to the XYZ orthogonal coordinate system.

In this preferred embodiment, as shown in FIG. 1, the left-hand direction is referred to as a (+X) direction, the rear direction is referred to as a (+Y) direction, and the vertically upward direction is referred to as a (+Z) direction in a case where the subject faces the support column 50. In addition, in a case where the X-ray generating part 10 and the X ray detection part 20 are viewed from above in a plan view, the direction from the X-ray generating part 10 toward the X-ray detection part 20 is referred to as a (+y) direction, the right-hand direction from the (−y) side to the (+y) side is referred to as a (+x) direction, and a vertically upward direction is referred to as a (+z) direction.

Further, X, Y, Z, x, y and z are used below for defining two-dimensional coordinates or planes. For example, the two-dimensional coordinates formed by the X-coordinate and Y-coordinate are referred to as XY coordinates, and the two-dimensional plane extending in the X direction and Y direction is referred to as an XY plane in some cases.

The X-ray generating part 10 and the X-ray generating part 20 are respectively fixed to both ends of the revolution arm 30 in a suspended manner and are supported so as to be opposed to each other. The revolution arm 30 is fixed to the elevator part 40 in a suspended manner through the revolution shaft 31 extending in the vertical direction.

The X-ray generating part 10 includes, inside a housing thereof, an X-ray generator 13 having an X-ray tube that is an X-ray source therefor. The housing of the X-ray generating part 10 is rotatably mounted to the support part 300 around the Z-axis. This rotation function is used in, for example, cephalic imaging (see FIG. 2).

The X-ray detection detection part 20 includes an X-ray detector 21 that detects X-rays that have passed through the object M1. The X-ray detector 21 forms an image sensor composed of a plurality of X-ray detection elements that are arranged so as to spread on a two-dimensional plane (herein, xz plane). The X-ray detection element outputs a signal corresponding to the intensity of the X-ray toward the outside. The image sensor obtains the intensity of the X-ray entering the X-ray detection part 20, at a frame rate needed, as frame image data (image information) in which each pixel has a pixel value corresponding to the intensity of the X-ray.

While the support part 300 is configured as the revolution arm 30 that revolves about the revolution shaft 31 and the X-ray generating part 10 and the X-ray detection part 20 are respectively mounted to both ends of the revolution arm 30 having an approximately rectangular solid shape in this preferred embodiment, the configuration of the support part 300 that supports the X-ray generating part 10 and the X-ray detection part 20 is not limited thereto. The X-ray generating part 10 and the X-ray detection part 20 may be supported so as to be opposed to each other by, for example, an annular member that rotates about the center of an annularly-shaped portion.

The elevator part 40 is engaged with the support column 50 vertically arranged so as to extend along the vertical direction. An upper fame 41 and a lower frame 42 of the elevator part 40 project toward the side opposite to the side on which the elevator part 40 is engaged with the support column 50, and thus the elevator part 40 has an approximately U-shaped structure.

An upper end portion of the revolution arm 30 is mounted to the upper frame 41 of the elevator part 40. The revolution arm 30 is suspended from the upper frame 41 of the elevator part 40 in this manner, and the revolution arm 30 is moved up and down as a result of the elevator part 40 moving along the support column 50.

The lower frame 42 of the elevator part 40 is provided with an object fixing part 421 composed of a rod for fixing the object M1 (in this case, human head) from the right and left sides, a chin rest for fixing a chin, and the like. The head of the subject is fixed such that the front-and-back direction of the head is parallel to or substantially parallel to the Y-axis direction. In other words, in the state in which the head is fixed, the median sagittal cross-section of the head is parallel to or substantially parallel to the YZ plane defined by the Y-axis direction and the Z-axis direction.

The revolution arm 30 is moved up and down in accordance with the height of the object M1 as well as in accordance with the moving up and down motions of the elevator part 40 so as to be adjusted to an appropriate position, so that the object M1 is fixed to the object fixing part 421 in that state. In the example shown in FIG. 1, the object fixing part 421 fixes the object M1 such that the direction of the body axis of the object M1 is identical to or substantially identical to the axial direction of the revolution shaft 31.

As shown in FIG. 1, the main-body control part 60 that controls the operations of the respective components of the main-body unit 1 is provided in the X-ray detection part 20. Further, the respective components of the main body unit 1 are accommodated in an X-ray proof room 70. A display part 61 and an operation panel 62 are provided on the outside wall of the X-ray proof room 70. The display part 61 is configured as, for example, a liquid crystal monitor for displaying various types of information based on the control of the main-body control part 60. The operation panel 62 is configured as, for example, buttons for inputting various commands to the main-body control part 60. The operation panel 62 is also used for designating, for example, the position of an image area of a living organ or the like. There are various modes (such as panoramic X-ray tomography, CT imaging and cephalic imaging) in X-ray imaging, and a mode to be executed can be selected through operation of the operation panel 62.

Provided on the back side of the X-ray detector 21 of the X-ray detection part 20 of the main body unit 1 are an operation panel 62A having a function same as or similar to that of the operation panel 62 and a display part 61A having a function same as or similar to that of the display part 61, so that the main body unit 1 can be operated from the inner side and the outer side of the X-ray proof room 70.

The information processing device 8 includes an information processing main body 80 configured as a computer, a work station, or the like, and is capable of sending/receiving various types of data to/from the main body unit 1 by means of a communication cable. Data can be exchanged between the main body unit 1 and the information processing device 8 in a wireless manner.

A display part 81 of the information processing device 8 is configured as a display device such as a liquid crystal monitor and an operation part 82 is composed of a keyboard, a mouse, and the like, and these display part 81 and the operation part 82 are connected to the information processing main body 80. An operation is capable of providing various commands to the information processing device 8 by means of the operation part 82. It is also possible to configure the display part 81 as a touch panel and, in this case, the display part 81 performs a part or the entirety of the functions of the operation part 82.

FIG. 2 is a front view showing a cephalostat 43 applicable to the panoramic tomography X-ray apparatus 100. As shown in FIG. 2, the cephalostat 43 may be provided on the elevator part 40. The cephalostat 43 is mounted to, for example, an arm 501 extending from the middle portion of the support column 50 in the horizontal direction. The cephalostat 43 is provided with a fixture 431 for fixing the head of a patient at a fixed position and an X-ray detector 432 for cephalic imaging. Various cephalostats such as one disclosed in Japanese Patent Application Laid-Open No. 2003-245277 are adoptable as the cephalostat 43.

FIG. 3 is a block diagram of the configuration of the panoramic tomography X-ray apparatus 100.

As shown in FIG. 3, the main body unit 1 includes a driving part 65 composed of a revolution motor 60R, an X-axis motor 60X, and a Y-axis motor 60Y. The X-axis motor 60X and the Y-axis motor 60Y cause the revolution shaft 31 to move horizontally in the X-axis direction and the Y-axis direction by means of an X-Y movement mechanism composed of an X-direction movement mechanism (not shown) and a Y-direction movement mechanism (not shown). The X-direction movement mechanism is formed of a mechanical component that displaces the revolution shaft 31 in the X-axis direction relative to the object M1, and the Y-direction movement mechanism is formed of a mechanical component that displaces the revolution shaft 31 in the Y-axis direction relative thereto. In addition, the revolution motor 60R rotates the revolution shaft 31 about the Z-axis by means of a revolution mechanism (not shown) composed of a mechanical component that rotates the revolution shaft 31 relative to the object M1. In other words, the driving part 65 causes the revolution arm 30 to move horizontally or move while revolving relative to the object M1 located at a position needed. In this preferred embodiment, the driving part 65, the revolution shaft 31, and the support part 300 (revolution arm 30) constitute the revolution mechanism.

The main-body control part 60 has a configuration of a typical computer, in which a CPU 601, a storage part 602, a ROM 603, and a RAM 604 are connected to a bus line. The CPU 601 executes various control programs including a program PG1 for controlling the driving part 65, and the storage part 602 is formed as a fixed disk such as a hard disk and stores various types of data and the program PG1.

The CPU 601 executes the program PG1 stored in the storage part 602 on the RAM 604, and accordingly functions as an X-ray generating part control part 601a that controls the X-ray generating part 10 and an X-ray detection part control part 601b that controls the X-ray detection part 20 in accordance with various imaging modes. The X-ray generating part control part 601a is also capable of controlling an irradiation amount of X-rays and has the function of the X-ray irradiation control part. In addition, the CPU 601 functions as a driving control part 601c that controls driving of the driving part 65 and, for example, controls driving such that, for example, the X-ray generating part 10 and the X-ray detection part 20 are moved in a track in accordance with various types of imaging.

The CPU 601 forming the main-body control part 60 and a CPU 801 forming the information processing main body 80 collectively constitute a control system.

The operation panel 62 connected to the main-body control part 60 is composed of a plurality of operation buttons and the like. As an input device used in place of or used together with the operation panel 62, a keyboard, a mouse, a touch pen, and the like are adoptable in addition to the operation button. Alternatively, recognition may be made upon reception of a voice command by a microphone or the like. That is, the operation panel 62 is just an example of the operation means (operation part). Therefore, any operation means may be adopted as long as the operation of the operator can be received. Still alternatively, the display part 61 may be formed of a touch panel and, in this case, the display part 61 has a part or the whole of the functions of the operation panel 62.

Various types of information required for the operation of the main body unit 1 are displayed on the display part 61 in the format of text, image, and the like. Note that the display contents displayed on the display part 81 of the information processing device 8 may also be displayed on the display part 61. Alternatively, various commands may be issued to the main body unit 1 through, for example, a pointer operation with a mouse or the like on the text or image displayed on the display part 61.

An adjustment part 601d specifies the position of the object M1, and adjusts the tracks of the X-ray generator 13 and the X-ray detector 21 being revolving, in accordance with the specified position of the object M1. Conceivable examples of the method of specifying the position of the object M1 include one that uses a laser beam. Specifically, a laser beam is emitted from a position detection part 17 (in this case, laser light source) included in the X-ray generating part 10, and the X-ray generating part 10 is moved such that a characteristic position of the face of the subject is irradiated with laser beam. For example, if positions on corners of the lips of the subject are irradiated with a laser beam, the positions of canine teeth that are part of a dentition can be roughly specified. This enables to roughly specify, that is, detect the position of the dentition of the object M1. The revolving tracks of the X-ray generator 13 and the X-ray detector 21 are adjusted (shifted) based on the positional information being detection results obtained through the specification and detection as described above. As a result, the positional relationship among the X-ray generator 13, the X-ray detector 21, and the object M1 is appropriately adjusted, which enables to perform panoramic X-ray tomography.

Conceivable modes in which position adjustment is performed include a mode in which one of the X-ray generator 13 and the X-ray detector 21 moves relative to the object M1 and a mode in which the X-ray generator 13 and the X-ray detector 21 both move relative to the object M1. In any case, the positional relationship among the object M1, the X-ray generator 13, and the X-ray detector 21 is adjusted.

The main body unit 1 takes an image of an area of interest (such as living organ, bones including teeth, and joint) of the object M1 with X-rays in accordance with the operation panel 62 or the command from the information processing device 8. In addition, the main body unit 1 receives various commands, coordinate data, and the like from the information processing device 8 and, on the other hand, transmits the X-ray projection data obtained by imaging to the information processing device 8. In this preferred embodiment, in the main body unit 1, an image of a dentition 90 as shown in FIG. 6 is taken, so that panoramic X-ray tomography of an area of the dentition is thus performed.

The information processing main body 80 has a configuration of a typical computer, in which a CPU 801, a storage part 802, a ROM 803, and a RAM 804 are connected to a bus line. The CPU 801 executes various programs, and the storage part 802 is formed of a fixed disk such as a hard disk and stores various types of data and a program PG2.

The CPU 801 executes the program PG2 stored in the storage part 802 on the RAM 804 to function as a position setting part 801a and an image information processing part 801b. The position setting part 801a sets a position of a tomographic plane in generating a panoramic tomography X-ray image, based on an input of the operation via the operation part 82. The setting of the position of the tomographic plane is described below in detail. The image information processing part 801b generates a panoramic tomography X-ray image corresponding to the position of the tomographic plane from the frame image data obtained in the panoramic X-ray tomography. The generation of the panoramic tomography X-ray image is also described below in detail. The CPU 801 functions as the position setting part 801a and the image information processing part 801b, whereby the information processing device 8 functions as an image processing device.

The program PG1 and PG2 may be obtained by the main-body control part 60 or the information processing main body 80 via a predetermined network line or the like. Alternatively, the programs PG1 and PG2 stored in a portable medium (such as a CD-ROM) may be obtained by the main-body control part 60 or the information processing main body 80 by reading with a predetermined reader.

In this preferred embodiment, the operator designates the CT image area by the operation panel 62 or the operation part 82. Specifically, a screen (an illustration, a panoramic image or the like) displaying a part or the entirety of a living body appears on the display part 61 or the display part 81, and the operator designates the area desired to be imaged by the operation panel 62 or the operation part 82, whereby the image area is designated. Alternatively, in place of displaying a screen for specifying an area on the screen, a portion may be designated directly by input of the name of the portion or input of a code from the operation panel 62 or the operation part 82.

A control part may be additionally provided in the operation panel 62 to bear a part of the control by the main-body control part 60, or the main-body control part 60 may be provided on the entire surface of the operation panel 62.

<1.2. Panoramic X-Ray Tomography and Generation of Panoramic Tomography X-Ray Image>

In panoramic X-ray tomography, the X-ray generator 13 and the X-ray detector 21 are disposed so as to face each other with dentition of the object M1 sandwiched therebetween, and the X-axis motor, the Y-axis motor, and the revolution motor are driven such that the X-ray generator 13 and the X-ray detector 21 rotate about the object M1 in an integrated manner (see FIG. 3). The X-rays emitted from the X-ray generator 13 pass through an X-ray restriction part 16 (primary X-ray shielding part), and are then formed into the long and narrow X-ray beam BX1 that extends in the z-axis direction. An unnecessary scattering X-ray portion of the X-ray beam BX1 that has passed through the object M1 is partially shielded preferably by a collimator (secondary X-ray shielding part; not shown) that is provided on the front surface of the X-ray detector 21 and forms a narrow gap. Then, a portion of the X-ray beam BX1, which has passed through the narrow gap of the collimator, enters the X-ray detector 21.

In panoramic X-ray tomography, a standard dental arch (a horseshoe-shaped or approximately-horseshoe-shaped curve) is assumed in advance. The X-ray generator 13 moves such that the X-ray beam BX1 enters this dental arch almost perpendicularly thereto. Preferably, the X-ray detector 21 and the X-ray generator 13 are moved such that the moving track of the X-ray beam BX1 generates a symmetrical envelope track of an approximately triangular shape with respect to the vertex of the dental arch that projects toward the front tooth portion. The X-ray beam BX1 is radiated from one portion in the vicinity of the right or left jaw joint or back tooth toward the front tooth of a dental arch and then from the front tooth toward the other portion in the vicinity of the right or left jaw joint or back tooth thereof, and pieces of frame image data on the irradiated portions are incessantly and continuously obtained by the X-ray detector 21. The above-mentioned movement of the X-ray generator 13 is disclosed in, for example, Japanese Patent Application Laid-Open No. 2009-131656 (for example, see FIG. 5) filed by the applicant of the present application.

The pieces of image information each having a pixel value corresponding to the intensity of incoming X-rays are successively collected by the X-ray detector 21 at a frame rate needed and are accumulated and stored in the storage part 802. The image information processing part 801b reconfigures a panoramic tomographic image using the collected pieces of frame image data. Specifically, the process (process of adding pixel values (shift addition process)) of successively superimposing overlapped portions of images on the consecutive frame images is performed along the tomographic plane corresponding to the dental arch that has been set. As a result, a single panoramic tomographic image is generated. Various techniques of the shift addition process have been proposed, and it is possible to appropriately apply such techniques also in the present invention.

A MOS sensor or a CMOS sensor may be preferably used as the X-ray detector 21, which may be any electrical imaging sensor as long as a frame image is obtained. In other words, various sensors including a flat panel detector (FPD) such as a CCD sensor, and a solid-state imaging element can be used.

In order to obtain a clear panoramic tomography X-ray image with little blurring for an area that an image reader wants to view, it is required to appropriately set a position of a tomographic plane. In the shown preferred embodiment, the position setting is performed via a GUI.

FIG. 4 is a view showing a display screen for position setting W1. The display screen W1 corresponds to the entire screen of the display part 81 or a predetermined display window that appears on the entire screen of the display part 81. As shown in FIG. 4, an image for position designation PA11 is displayed on the display screen W1. For the sake of description, a cross-sectional view (cross-sectional view of a dentition) when the portions corresponding to front teeth FT1 of an upper jaw and front teeth FT2 of a lower jaw of the dentition 90 of the object M1 are cut on the YZ plane is shown on the right side of the display screen W1 in FIG. 4.

The image for position designation PA11 shown in FIG. 4 is a standard panoramic tomographic image P1. The standard panoramic tomographic image P1 is a tomographic image generated by performing the process of adding images along a standard tomographic plane FS1 set in advance. The standard tomographic plane FS1 has, for example, a standard shape and corresponds to a dentition model having a standard size. That is, the standard tomographic plane FS1 has a curved shape parallel to the Z-axis extending along the dental arch of this dentition model, which is a curved plane so as to be curved into a horseshoe shape in top plane view (see FIGS. 7A and 7B). Therefore, the standard tomographic plane FS1 does not necessarily correspond to the dentition shape of the object M (subject) completely, which roughly has a shape corresponding thereto.

Here, as shown in the cross-sectional view of the dentition, a typical dentition extends so as to be inclined forward (toward the (−Y) direction opposite to the depth direction (+Y) direction)) at the portions of the front teeth FT1 of the upper jaw and the front teeth FT2 of the lower jaw. On the other hand, the standard tomographic plane FS1 has a shape to be parallel to the Z-axis direction, which does not correspond to the shape of the portion in the vicinity of the front teeth of the dentition of the object M1. Accordingly, in a case of the standard panoramic tomographic image P1 reconfigured based on the standard tomographic plane FS1, a tomographic image may be blurred and unclear.

Therefore, in this preferred embodiment, position setting is performed in order that the standard tomographic plane FS1 for reconfiguring a panoramic tomographic image will turn into a desired tomographic plane (tomographic plane FS2). For that purpose, first, the standard panoramic tomographic image P1 is displayed on the display part 81 as the image for position designation PA11, and three partial area frames F1, F2, and F3 for designating the position are displayed on the standard panoramic tomographic image P1. The image for position designation PA11 is an example of images constituting an image for position setting that is used in setting of a position of the tomographic plane.

The partial area frames F1, F2, and F3 are frames that define partial areas smaller than the image for position designation PA11. The partial area frames F1, F2, and F3 are provided for adjusting the position regarding the depth direction (position in the Y-axis direction) of the tomographic plane (tomographic plane FS2) based on a predetermined operation by the operator, as described below. The partial area frames F1, F2, and F3 may be each set so as to move in the direction orthogonal to the depth direction, specifically, move longitudinally (corresponding to the Z-axis direction) along a median line L1 defined on the image for position designation PA11, based on a predetermined operation by an operator. In addition, the partial area frames F1, F2, and F3 may also be set so as to move laterally (corresponding to the direction in which the standard tomographic plane FS1 extends) in the range including the median line L1.

An object having standard body shape (a human being body) is substantially symmetric in right and left, and the median line L1 being a straight line coincides with an axis of symmetry of the object that is substantially symmetric in right and left viewed from the front (or viewed from the rear). The median line L1 is also a center line between the right side and left side of the object being substantially symmetric viewed from the front. The median portion refers to a portion including the axis of symmetry. When the median plane of the object is called a median plane MP, the median plane MP looks a straight line when viewed from the front, and when this straight line is called a line ML, the median line L1 is a line coincides with the line ML. In the present invention, a head of a human being is especially paid attention, and the median portion is the portion of a dental arch, jaws, a face intersecting the median line L1 and containing the median line L1 viewed from the front. And also the median portion is a portion of a dental arch, jaws, a face intersecting the median plane MP and containing the median plane MP. The median portion refers to a portion including the axis of symmetry. Specifically, when viewed from the front, the human head is substantially symmetric, and the axis of symmetry passes through the front teeth of the upper jaw and the front teeth of the lower jaw. That is, the straight line passing through the front teeth of the upper jaw and the front teeth of the lower jaw serves as the median line L1. The portion including the front teeth of the upper jaw and the lower jaw is defined as the median portion.

The partial area frames F1, F2, and F3 are set for the partial areas including at least the median portion. The partial area frames F1, F2, and F3 may be set so as to move to the positions offset from the median portion, which are configured to be positioned in the partial areas including at least the median portion. If the partial area frames are moved, partial panoramic tomographic images described below are generated regarding the locations to which the partial area frames have moved.

In this preferred embodiment, the position of the tomographic plane for reconfiguring a panoramic tomographic image including the entire dentition is set by adjusting the position (position in the Y-axis direction) regarding the depth direction of the tomographic plane corresponding to the partial area frames F1, F2, and F3. More specifically, the position regarding the depth direction of the tomographic plane (partial tomographic planes FSF1, FSF2, and FSF3) corresponding to the partial area frames F1, F2, and F3 is changed through a predetermined operation. This operation may be performed, for example, by the operation of moving a pointing device such as a mouse, or by inputting numeric values by means of a keyboard.

More specifically, any of the partial area frames F1, F2, and F3 may be selected through the operation of clicking a mouse such that the selected partial area frame is adjusted, by a roller included in a recent mouse, to be positioned in the +Y depth direction through a rotational operation to one of the + and − rotational directions and be positioned in the −Y depth direction through a rotation operation to the other of the + and − rotational directions.

FIG. 5 is a view showing the display screen W1 when the positions in the depth direction of the partial tomographic planes FSF1 to FSF3 are changed. In the initial state, the partial tomographic planes FSF1 to FSF3 are set to the same positions as those of the standard tomographic plane FS1 regarding the depth direction (see cross-sectional view of the dentition in FIG. 4). Then, the above-mentioned predetermined operation is performed, and accordingly, the partial tomographic planes FSF1 to FSF3 are moved back and forth in the depth direction, so that the positions thereof are designated.

When the partial tomographic planes FSF1 to FSF3 are moved, a tomographic image of the tomographic plane corresponding to the positions of the partial tomographic planes FSF1 to FSF3, in this case, partial panoramic tomographic images PF1, PF2, and PF3 passing through the positions of the partial tomographic planes FSF1 to FSF3 are generated, respectively. The partial panoramic tomographic images PF1 to PF3 are generated in the same manner as, for example, the standard panoramic tomographic image P1. However, the sizes of the generated images are equal to the sizes of the partial tomographic planes FSF1 to FSF3. In other words, the partial panoramic tomographic images PF1 to PF3 have the sizes defined by the partial area frames F1 to F3. The generated partial panoramic tomographic images PF1 to PF3 are displayed on the partial area frames F1 to F3 in a superimposed manner. Accordingly, new partial panoramic tomographic images PF1 to PF3 are generated and are displayed on the partial area frames F1 to F3 in a superimposed manner every time the positions in the depth direction of the partial tomographic planes FSF1 to FSF3 are changed. The partial panoramic tomographic images PF1 to PF3 are examples of the X-ray image of the median portion (that is, median-portion X-ray image), which constitute an image for position setting together with the image for position designation PA11. The median portion is imaged in the partial panoramic tomographic images PF1 to PF3, and the partial panoramic tomographic images PF1 to PF3 are median-portion X-ray images including the median portion. In the present invention, the images constituting the image for position setting, such as the image for position designation PA11 and the partial panoramic tomographic images PF1 to PF3, are referred to as images forming an image for position setting.

The partial panoramic tomographic images PF1 to PF3 are the median-portion X-ray images that display the position for designating the tomographic plane in the depth direction (Y-axis direction) of the median portion.

In the present invention, the median-portion X-ray image (specifically, X-ray image of the tomographic plane of the median portion) such as the partial panoramic tomographic images PF1 to PF3 that are used in setting of a position of the tomographic plane of the median portion, or an X-ray image showing the tomographic plane of a specific position regarding the depth direction in the median portion is a median-portion tomographic plane position specifying image.

In this preferred embodiment, a panoramic tomographic image to be newly generated when the positions in the depth direction of the partial tomographic planes FSF1 to FSF3 are changed is limited to a partial one. Therefore, an amount of computation process required for generating an image can be reduced compared with the case of newly generating a panoramic tomographic image (for example, standard panoramic tomographic image P1) including the entire dentition.

A reduced amount of computation process enables to generate the partial panoramic tomographic images PF1 to PF3 in real time. That is, the operation of moving the partial tomographic planes FSF1 to FSF3 by the operator is reflected in the partial panoramic tomographic images FSF1 to FSF3 immediately after the operation is received. This allows the operator to accurately stop the partial tomographic planes FSF1 to FSF3 at desired positions.

For example, in the example shown in FIG. 5, the partial tomographic plane FSF1 is set to a position at which it has moved in the depth direction with respect to the standard tomographic planes FS1 by a distance needed. In addition, a position in the longitudinal direction of the partial area frame F1 is set on the image for position designation PA11 such that the partial area frame F1 includes a tooth root portion RT1 of the front teeth FT1 of the upper jaw. The front teeth FT1, particularly a root apex portion RTe1 thereof located in the root of the tooth root portion RT1 or the portion in the vicinity thereof, effectively serves as an indicator in setting the position of a tomographic plane for obtaining a panoramic tomographic image. That is, a position of the tomographic plane FS2 of a panoramic tomographic image in which a portion in the vicinity of the tooth root portion RT1 becomes clear can be set by setting the position of the partial tomographic plane FSF1 to make the tooth root portion RT1, particularly root apex portion RTe1 or the edge in the vicinity thereof, clear.

In the example shown in FIG. 5, the partial tomographic plane FSF3 is set to a position at which it has moved in the depth direction with respect to the standard tomographic plane FS1 by a distance needed. In addition, the height position of the partial area frame F3 is set on the image for position designation PA11 such that the partial area frame F3 includes a tooth root portion RT2 of the front teeth FT2 of the lower jaw. The front teeth FT2, particularly a root apex portion RTe2 thereof located in the root of the tooth root portion RT2 or the portion in the vicinity thereof, effectively serves as an indicator in adjusting a focus, similarly to the above-mentioned root apex portion RTe1 of the tooth root portion RT1. That is, it suffices that a position in the depth direction of the partial tomographic plane FS3 is set in a panoramic tomographic image PF3 to make the root apex portion RTe2 of the tooth root portion RT2 or the edge in the vicinity thereof clear. Accordingly, it is possible to finely set the position of the tomographic plane FS2 of the panoramic tomographic image that has a clear image quality for the portion in the vicinity of the tooth root RT2.

In addition, in the example shown in FIG. 5, the partial area frame F2 is set to a position at which it has moved in the direction (that is, front side of a subject) opposite to the depth direction with respect to the standard tomographic plane FS1 by a distance needed. The position in the longitudinal direction of the partial area frame F2 is set on the image for position designation PA11 such that the partial area frame F2 includes a tooth crown portion CT1 and a tooth crown portion CT2 of the front teeth FT1 and FT2. Similarly to the root apex portion RTe1 of the tooth root portion RT1, a tip portion CTe1 or a CTe2 of the tooth crown portion CT1 or the tooth crown portion CT2 effectively serves as an indicator in adjusting a focus. In other words, the position in the depth direction of the partial tomographic plane FSF2 is set such that the front teeth FT1 and FT2, particularly the tip portion CTe1 or tip portion CTe2, or an edge in the vicinity thereof can be clearly identified in the partial panoramic tomographic image PF2. Accordingly, a position of the tomographic plane FS2 for generating a panoramic tomographic image having a clear image quality can be finely set for an occlusion portion (tip portions CTe1 and CTe2 of the tooth crown portions CT1 and CT2, that is, tip portions of the teeth or the portion in the vicinity thereof).

From the above, the root apex portion RTe1 or the vicinity thereof, the root apex portion RTe2 or the vicinity thereof, or the tip portions CTe1 and CTe2 or the vicinities thereof effectively serve as an indicator in adjusting a focus. Therefore, preferably, the positions in the X-axis direction and the Z-axis direction of the partial tomographic plane FSF1 are set so as to include the root apex portion RTe1 or the vicinity thereof when being moved in the Y-axis direction. Similarly, the positions in the X-axis direction and the Z-axis direction of the partial tomographic plane FSF3 are set so as to include the root apex portion RTe2 or the vicinity thereof when being moved in the Y-axis direction. Further, the positions in the X-axis direction and the Z-axis direction of the partial tomographic plane FSF2 are set so as to include the tip portions CTe1 and CTe2 or the vicinities thereof when being moved in the Y-axis direction.

While three partial area frames are provided in the examples shown in FIG. 4 and FIG. 5, only frames less than three may be provided. For example, only any one of the partial area frames F1 to F3 shown in FIG. 4 and FIG. 5 may be provided or only any two of them may be provided.

For example, only the partial area frame F1 may be provided so as to adjust the position of the tomographic plane for only the front teeth FT1 of the upper jaw, specifically, for only the tooth root portion RT1 of the front teeth FT1 of the upper jaw. Alternatively, only the partial area frame F3 may be provided so as to adjust the position of the tomographic plane for only the front teeth FT2 of the lower jaw, specifically, for only the tooth root portion RT2 of the front teeth FT2 of the lower jaw. Still alternatively, only the partial area frames F1 and F3 may be provided so as to adjust the position of the tomographic plane for only the tooth root portion RT1 of the front teeth FT1 of the upper jaw and the tooth root portion RT2 of the front teeth FT2 of the lower jaw. The tooth root portion cannot be checked visually, and thus, it is particularly highly effective to generate a tomographic image at an appropriate position. Needless to say, a more suitable tomographic image can be generated also with the use of the partial area frame F2. On the contrary, the number of frames may be increased such that partial area frames exceeding three may be provided.

The standard panoramic tomographic image P1 at the position along the standard tomographic plane FS1 may be continuously used for the image for position designation PA11. Alternatively, after the positions in the depth direction of the partial tomographic planes FSF1 to FSF3 are adjusted, a panoramic tomographic image of the tomographic plane FS2 that corresponds to the positions of the partial tomographic planes FSF1 to FSF3 after the position adjustment may be generated once, and the panoramic tomographic image once generated may be used as a new image for position designation PA11.

In the present invention, the panoramic tomographic image of the tomographic plane FS2, which is generated after the position adjustment in the depth direction of the partial tomographic planes FSF1 to FSF3 and corresponds to the positions of the partial tomographic planes FSF1 to FSF3 after the position adjustment, is referred to as an adjusted panoramic tomographic image.

In a case where the adjusted panoramic tomographic image generated and displayed as a result of the position adjustment in the depth direction of the partial tomographic planes FSF1 to FSF3 by the operator is judged to be poor, the adjusted panoramic tomographic image displayed once may be used as a new image for position designation PA11. Alternatively, upon instruction for reset, which is set to be received, the normal panoramic tomographic image P1 at the position along the initial normal tomographic plane FS1 may be displayed again as the image for position designation PA11.

FIG. 6 is a view showing the positional relationship between the dentition 90 of the object M1 and the standard tomographic plane FS1 or the newly-set tomographic plane FS2. The left side of FIG. 6 is a plan view of the dentition 90 of the lower jaw, and the right side of FIG. 6 is a cross-sectional view of the dentition as in FIG. 5. The plane view on the left side of FIG. 6 shows a portion (curve) of the tomographic plane FS2 passing through a position Pos2 of the partial tomographic plane FSF2 and a position Pos3 of the partial tomographic plane FSF3.

As described with reference to FIG. 5, if the positions in the depth direction of the partial tomographic planes FSF1 to FSF3 are set, a position of the tomographic plane FS2 is set based on the set positions. Specifically, as shown in the cross-sectional view of the detention in FIG. 6, the tomographic plane FS2 is set so as to pass through the position Pos1 of the partial tomographic plane FSF1, the position Pos2 of the partial tomographic plane FSF2, and the position Pos3 of the partial tomographic plane FSF3.

The panoramic tomographic image of the partial tomographic plane FSF2 includes image information of the portion in the area PA2 extending toward the tongue-side direction (inwardly from the dentition) or the cheek-side direction (outwardly from the dentition). That is, the panoramic tomographic image of the partial tomographic plane FSF2 has a tomographic thickness shown in the area PA2. Similarly, the partial tomographic plane FSF3 includes image information of the portion in the area PA3 extending toward the tongue-side direction and the cheek-side direction. That is, the panoramic tomographic image of the partial tomographic plane FSF3 has a tomographic thickness shown in the area PA3.

Here, the position in the depth direction of the position Pos2 is matched with those of the tip portions CTe1 and CTe2 of the front teeth FT1 and FT2. The positions Pos1 and Pos3 are matched with those of the root apex portions RTe1 and RTe2 of the front teeth FT1 and FT2. Accordingly, the position Pos2 is disposed in the front side of the subject with respect to the positions Pos1 and Pos3. Therefore, the position of the tomographic plane FS2 passing through the positions Pos1 to Pos3 changes in a non-linear manner (in this case, into a beak shape) regarding the depth direction, along the median line parallel to the Z-axis direction.

While in determining the tomographic plane FS2 passing through the positions Pos1 to Pos3, the positions Pos1 to Pos3 are linearly connected to each other in YZ cross-section in the example shown in FIG. 6, the positions Pos1 to Pos3 may be connected to each other with a curved line. Preferably, as in the state shown in the view on the right side of FIG. 6, the position Pos2 is set such that the line connecting the position Pos1 and the position Pos2 passes through the tooth axis of the front teeth FT1 and that the line connecting the position Pos2 and the position Pos3 passes through the tooth axis of the front teeth FT2.

In this preferred embodiment, the position in the depth direction is set in the front teeth FT1 and FT2 of the upper jaw and lower jaw and the occlusion portion thereof. However, the tomographic plane FS2 may be automatically set so as to pass through a position in the depth direction after the position is set for at least one of them. On this occasion, it is possible to support the shape of the portion in the vicinity of the front teeth if the tomographic plane is set so as to change in a non-linear manner (for example, into a beak shape) regarding the depth direction along the median line L1.

In this preferred embodiment, an operator manually designates the positions of the partial tomographic planes FSF1 to FSF3 while checking the partial panoramic tomographic images PF1, PF2, and PF3 displayed on the image for position designation PA11 in a superimposed manner. However, it is also possible to automate those operations by predetermined image recognition. For example, in a case of setting the position of the partial tomographic plane FSF1, the position of the partial tomographic plane FSF1 when the above-mentioned edge of the root apex portion RTe1 of the front teeth FT1 of the upper jaw can be recognized may be automatically specified.

For example, in order to recognize the edge of the root apex portion RTe1 of the front teeth FT1, a plurality of tomographic images of the partial tomographic plane FSF1 are continuously generated back and forth in the Y direction being the depth direction of the root apex portion RTe1 of the front teeth FT1. Then, the sharpness of the edge of each tomographic image is measured, to thereby specify a position having high sharpness. Here, the sharpness may be recognized for all of the partial tomographic planes FSF1 to FSF3. Alternatively, only part of the partial tomographic planes FSF1 to FSF3 may be recognized and the position setting part 801a may receive the input of such selection. It suffices that the position of the tomographic plane FS2 is set automatically in this manner. While the tomographic image of the partial tomographic plane FSF1 that is an X-ray image of the median portion is generated for edge recognition and used in image recognition in the example above, this tomographic image is an example of images constituting the image for position setting.

As described above, the position of the tomographic plane FSF2 is set in the median portion including the median line L1, which enables to generate a panoramic tomographic image corresponding to the shapes of the front teeth FT1 and FT2 located in the vicinity of the median line L1 of the dentition 90.

Next, a description is given of the method of generating a panoramic tomographic image including the entire dentition 90 based on the tomographic plane FS2 that has been set.

Figure 7A:
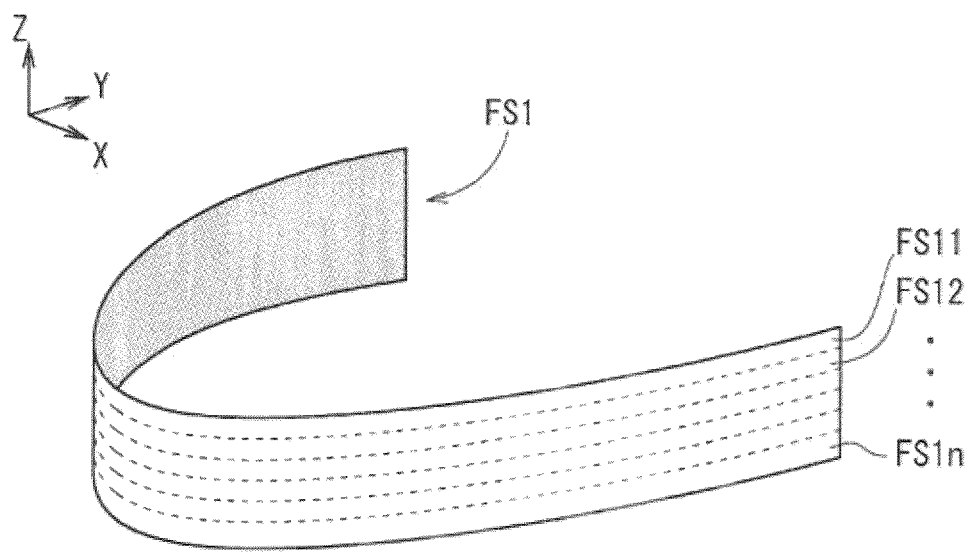
FIG. 7A is a view for explaining the principle of generating a panoramic tomographic image of a normal tomographic plane.
Figure 7B:
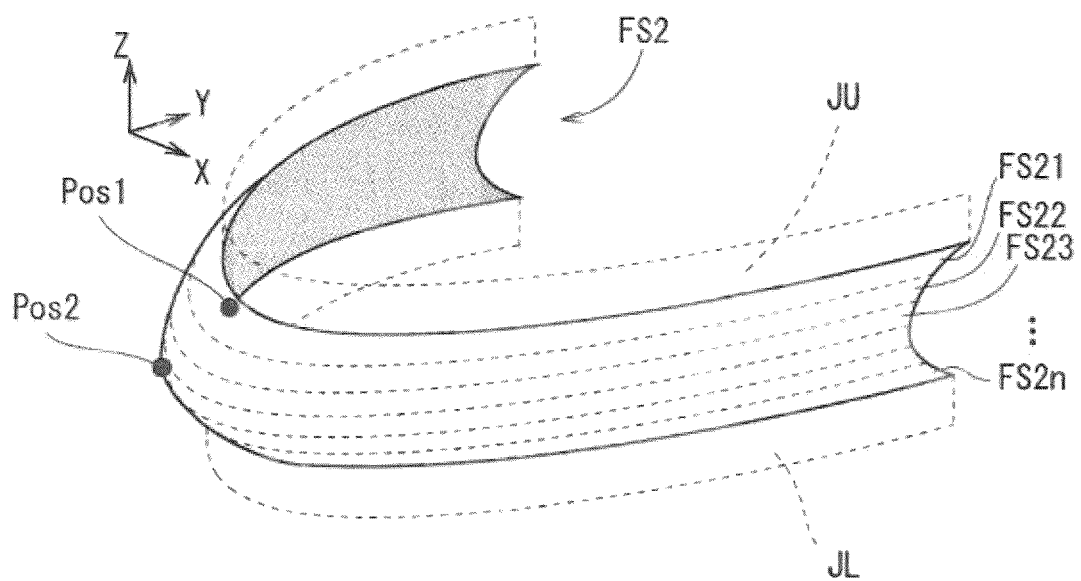
FIG. 7B is a view for explaining the principle of generating a panoramic tomographic image of a tomographic plane newly set.

FIG. 7A is a view for explaining the principle of generating a panoramic tomographic image of the normal tomographic plane FS1. FIG. 7B is a view for explaining the principle of generating a panoramic tomographic image of the tomographic plane FS2 newly set.

As shown in FIG. 7A, the standard tomographic plane FS1 is parallel to the Z-axis and has a surface curved into a horseshoe shape or an approximately horseshoe shape along the dental arch in top plane view. The standard tomographic plane FS1 shown in FIG. 7A is composed of a plurality of sections FS11 to FS1n along the Z-axis direction. The section FS11 to FS1n each pass through the same coordinates of the XY plane at different height positions in the Z-axis direction.

On the contrary, the newly-set tomographic plane FS2 shown in FIG. 7B has a shape to project toward the (−Y) direction as closer to the center portion thereof in the Z-axis direction. Desirably, the tomographic plane FS2 has a smooth curved plane as shown in FIG. 7B.

While FIG. 7B shows only the area occupied by the main body of teeth of the dental arch, which includes the portions corresponding to the front teeth FT1 and FT2 shown in FIG. 4 and FIG. 5, in outline with a solid line for easy understanding. In actuality, however, the tomographic plane corresponding to planes JU and JL, which extend above and below the front teeth FT1 and FT2 as shown in the view on the right side of FIG. 6, extends as indicated by broken lines (similarly, the tomographic plane corresponding to the planes JU and JL is assumed in FIG. 7A, which is not shown). It is desirable that the tomographic plane FS2 be made such that the outline portion by a solid line shown in FIG. 7B and the portions corresponding to the planes JU and JL are continuous from each other smoothly without a step therebetween.

Preferably, for each amount of one pixel in height in the Z-axis direction, pieces of image data on the curved shape of the dental arch, which are matched with the shape of the tomographic plane FS2, are generated and combined through an addition process from the frame image data, to thereby form a panoramic tomographic image regarding the entire tomographic plane FS2.

Now, looking at the positions of sections FS21 to FS2n having a curved shape of the dental arch at different heights in the Z-axis direction of the tomographic plane FS2 shown in FIG. 7B, which correspond to the sections FS11 to FS1n of the standard tomographic plane FS1 shown in FIG. 7A, respectively, the portion being the vertex of the projecting portion of the horseshoe shape projects toward the (−Y) direction.

The curvatures of the sections FS21 to FS2n can be set to be identical or almost identical to the curvatures of the sections FS11 to FS1n. This is because, as apparent from the comparison of the section FS21, the section FS23, and the like in FIG. 7B, in a case of tomographic plane data on a horseshoe shape or approximately horseshoe shape having the same curvature, effects of displacement are relatively small on the portions corresponding to the back teeth in section even if the position of part of the sections is displaced in the depth direction correspondingly to the front tooth, which makes the position of the tomographic layer unlikely to be offset from the original back tooth.

The tomographic plane FS2 may be formed such that the tomographic planes each having a width subdivided in the Z-axis direction and an elongated belt-like horseshoe shape are layered along the Z-axis. Even if pieces of image data on a curved shape of the dental arch are not generated by processing images starting from an appropriate position as needed, as long as the tomographic plane FS2 is set.

In the example above, the standard tomographic plane FS1 is set to be composed of the cross-sections FS11 to FS1n that are positioned at different heights in the Z-axis direction and at the same position in the XY plane, which is not limited thereto.

In the description above, mainly the case of panoramic tomography for entire area was explained, but the present invention can be applied to a partial panoramic tomography. For examples, the present invention can be applied to a panoramic tomography for one of a jaw area in right side and in left side.

Now, examples of setting of the positions of the partial tomographic planes FSF1, FSF2, and FSF3 and setting of the tomographic plane FS2 are specifically described.

FIG. 13A is a view showing an example of setting the position of the tomographic plane FS2 with the use of the partial tomographic planes FSF1 to FSF3. In the example shown in FIG. 13A, positions of specific points of the partial tomographic planes FSF1 to FSF3 are used as specific positions for determining the three-dimensional shape and position of the tomographic plane FS2. In the example shown in FIG. 13A, the partial tomographic planes FSF1 to FSF3 are rectangular, for example, square or oblong in shape, and an intersection point of lines connecting the centers of opposite sides is the specific position.

A specific position F1M, a specific position F2M, and a specific position F3M are set in the partial tomographic plane FSF1, the partial tomographic plane FSF2, and the partial tomographic plane FSF3, respectively. The specific positions F1M to F3M are set to be positioned at the median portion. The three-dimensional shape and position of the tomographic plane FS2 are determined by a line FS2L (described below, see FIG. 13B) passing through the specific positions F1M, F2M, and F3M at the median portion.

Figure 13B:
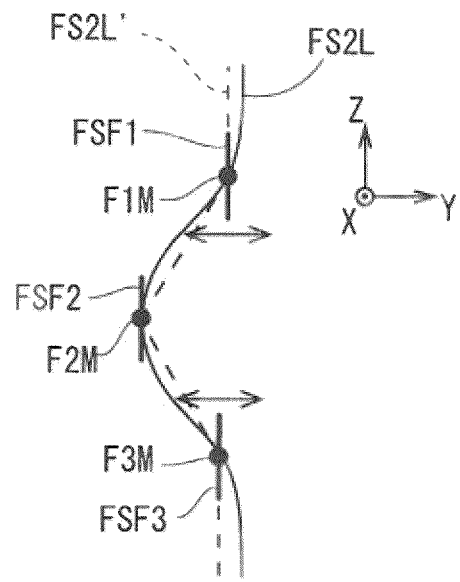
FIG. 13B is an end view showing a median portion of the tomographic plane FS2 shown in FIG. 13A, which is viewed from a −X side toward a +X side.

FIG. 13B is an end view showing the median portion of the tomographic plane FS2 shown in FIG. 13A, which is viewed from the −X side toward the +X side. FIG. 13B is also a view when the line FS2L is viewed from the −X side toward the +X side. As described above, the line FS2L passing through the median portion, which is indicated by a solid line, passes through the specific positions F1M, F2M, and F3M. A line FS2L' indicated by a broken line serves as the base for deriving the line FS2L as described below. The line FS2L is used for setting a position of a portion being the vertex of the projecting portion of the horseshoe shape composed of the cross-sections FS11 to FS1n described with reference to FIG. 7B.

In FIG. 13B, the lines FS2L' is formed of the straight line drawn from the upper portion of the upper jaw to the specific position F1M, the line segment connecting the specific positions F1M and F2M, the line segment connecting the specific positions F2M and F3M, and the straight line drawn from the specific position F3M to the lower portion of the lower jaw. The lines FS2L is based on the line FS2L', specifically, the line FS2L has a shape that is obtained through the correction in which the corner portions of the line FS2L', at which the line FS2L' changes its shape steeply, are rounded. Note that the line FS2L passes through the specific positions F1M to F3M, similarly to the line FS2L'.

Figure 13C:
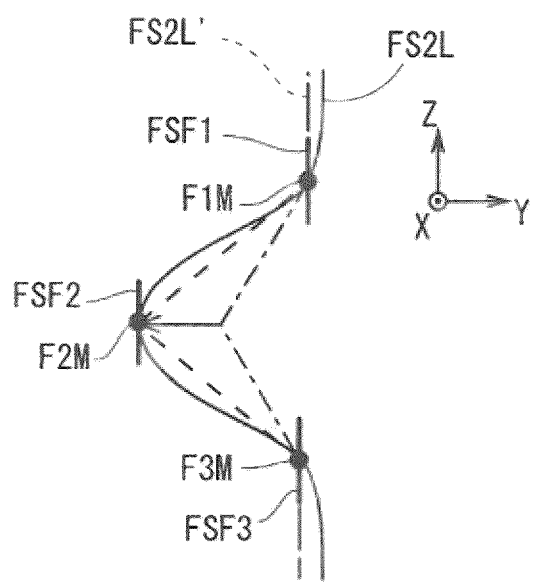
FIG. 13C is an end view showing a line FS2L to be set when the partial tomographic plane FSF2 shown in FIG. 13B is moved toward a −Y direction.

As described above, the positions of the partial tomographic planes FSF1 to FSF3 are each movable in the Y-axis direction. FIG. 13C is an end view showing the line FS2L to be set when the partial tomographic plane FSF2 shown in FIG. 13B is moved in the −Y direction. It is conceivable that as shown in FIG. 13C, for example, the partial tomographic plane FSF2 is further moved in the −Y direction so that the tomographic plane FS2 is deformed to have a shape in which the center portion thereof protrudes toward the −Y direction more. In FIG. 13C, the line FS2L' before being moved is indicated by a chain line, whereas the line FS2L' after being moved is indicated by a broken line.

Also in the example shown in FIG. 13C, the line FS2L is generated through the correction in which the corner portions of the line FS2L', at which the line FS2L' changes its shape steeply, are rounded. The line FS2L is used in setting a position of a tomographic plane. The specific positions F1M to F3M are positions for setting, which are provided for setting the final three-dimensional shape and position of the tomographic plane FS2. Similarly, the lines FS2L' and FS2L are lines for setting, which are provided for setting the final three-dimensional shape and position of the tomographic plane FS2.

Figure 14B:
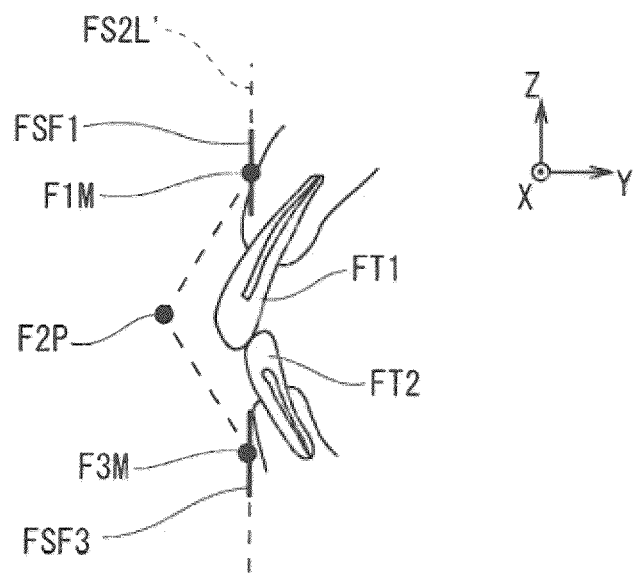
FIG. 14B is a view showing a median portion of the tomographic plane FS2 shown in FIG. 14A, with the addition of teeth to the end view when viewed from the −X side toward the +X side.

FIGS. 14A to 14F are views for explaining modifications of the manner of setting the position of the tomographic plane FS2 described with reference to FIGS. 13A to 13C. FIG. 14A is the view showing an example of setting the position of the tomographic plane FS2 with the use of the partial tomographic planes FSF1 and FSF3. In the modification shown in FIG. 14A, among the partial tomographic planes FSF1 to FSF3 used for setting of the tomographic plane FS2 shown in FIG. 13A, the partial tomographic plane FSF2 is omitted. This modification is advantageous in that a reduction of targets to be moved by the operator reduces a burden of the operation.

FIG. 14B is the view showing the median portion of the tomographic plane FS2 shown in FIG. 14A, with the addition of teeth to the end view when viewed from the −X side toward the +X side. FIG. 14B also shows the state when the line FS2L' indicated by a broken line is viewed the −X side toward the +X side. The state shown in FIG. 14B shows the state (for example, initial state) before the line FS2L' is moved and adjusted by the operator, which is the state in which the line FS2L' has not been set to an appropriate position.

Figure 14C:
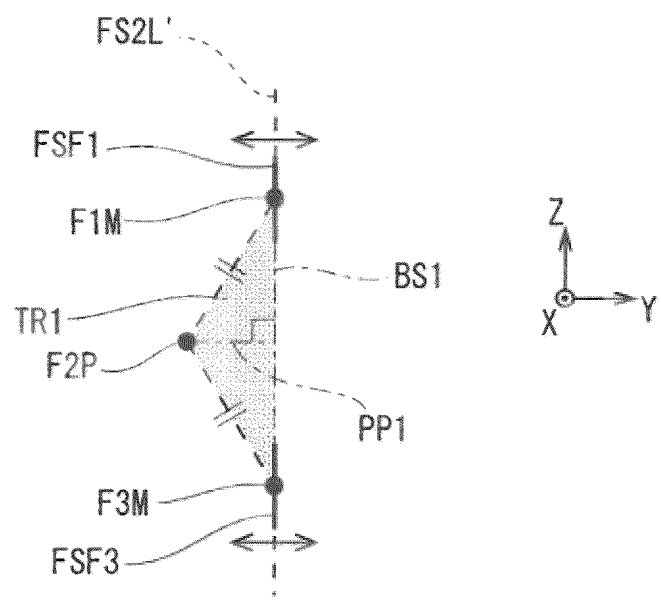
FIG. 14C is a view for explaining the shape of a line FS2L' shown in FIG. 14B.

FIG. 14C is the view for explaining the shape of the line FS2L' shown in FIG. 14B. FIG. 14C does not show the teeth. In this modification, as shown in FIG. 14C, a specific position F2P, which is determined from the positional relationship between the partial tomographic planes FSF1 and FSF3, specifically, the positional relationship between the specific positions F1M and F3M, is set. In this example, the specific position F2P is positioned at the vertex of an isosceles triangle having, as the base, a line segment BS1, which is indicated by a broken line connecting the specific positions F1M and F3M.

As shown in FIGS. 14B and 14C, the line FS2L' is formed of the straight line drawn from the upper portion of the upper jaw to the specific position F1M, the line connecting the specific positions F1M and F2P, and the straight line drawn from the specific position F3M to the lower portion of the lower jaw.

Figure 14D:
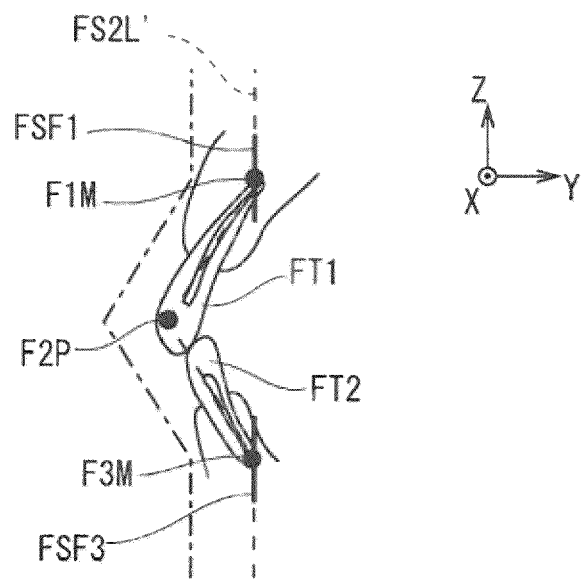
FIG. 14D is a view showing a state in which the partial tomographic plane FSF1 shown in FIG. 14C is moved in the +Y direction up to a position of a root apex portion of a front tooth FT1 of an upper jaw and the partial tomographic plane FSF3 shown in FIG. 14C is moved in the +Y direction up to a position of a root apex portion of a front tooth FT2 of a lower jaw.

FIG. 14D is the view showing a state in which the partial tomographic plane FSF1 shown in FIG. 14C is moved in the +Y direction up to a position of a root apex portion of the front tooth FT1 of the upper jaw and the partial tomographic plane FSF3 shown in FIG. 14C is moved in the +Y direction up to a position of a root apex portion of the front tooth FT2 of the lower jaw. Note that in FIG. 14D, the line FS2L' before being moved is indicated by a chain line, whereas the line FS2L' after being moved is indicated by a broken line.

Figure 14E:
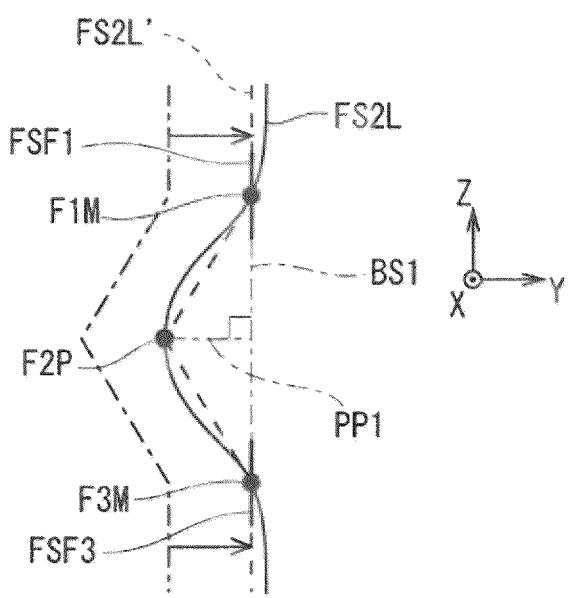
FIG. 14E is a view for explaining a shape of the line FS2L' shown in FIG. 14D.

FIG. 14E is the view for explaining a shape of the line FS2L' shown in FIG. 14D. FIG. 14E does not show the teeth. The line FS2L' shown in FIGS. 14D and 14E is set such that the specific position F1M is positioned at the root apex portion of the front tooth FT1 of the upper jaw, the specific position F2P is positioned at the tooth crown portion of the front tooth FT1 of the upper jaw and the tooth crown portion of the front tooth FT2 of the lower jaw, and the specific position F3M is positioned at the root apex portion of the front tooth FT2 of the lower jaw. That is, the line FS2L' is excellently shaped and positioned so as to pass through all of the root apex portion of the front tooth FT1 of the upper jaw, the tooth crown portion of the front tooth FT1 of the upper jaw, the tooth crown portion of the front tooth FT2 of the lower jaw, and the root apex portion of the front tooth FT2 of the lower jaw.

Further, as shown in FIG. 14E, the line FS2L' indicated by a broken line is subjected to the correction in which the corner portions thereof, at which the line FS2L' changes its shape steeply, are rounded, to t hereby generate the line FS2L indicated by a solid line. As described with reference to FIG. 7B, the line FS2L is used in setting the position being the vertex of the projecting portion of the horseshoe shape composed of the cross-sections FS11 to FS1n, as described with reference to FIG. 7B.

In this modification, even if the partial tomographic planes FSF1 and FSF3 are moved, the vertex of an isosceles triangle TR1 having, as the base, the line segment BS1 which is indicated by a broken line connecting the specific positions F1M and F3M is the specific position F2P. The length of a line segment PP1 (normal) indicated by a broken line vertically drawn from the specific position F2P being the vertex to the base BS1 is kept constant. The above-mentioned relationship is kept also in a case where only one of the partial tomographic planes FSF1 and FSF3 is moved.

Figure 14F:
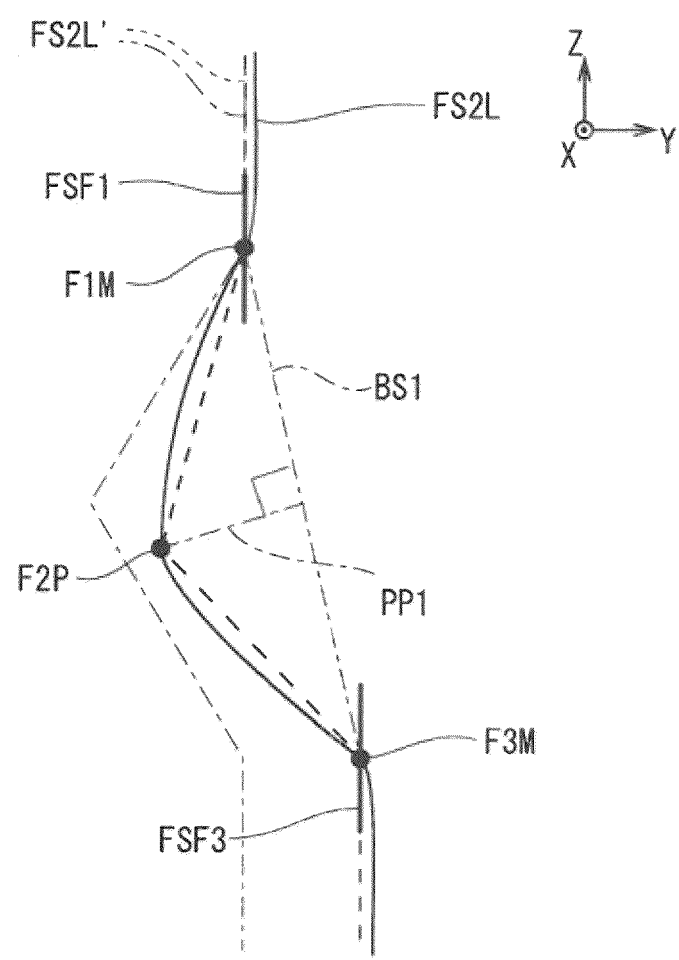
FIG. 14F is a view showing the lines FS2L' and FS2L when only the partial tomographic plane FSF3 is moved in the +y direction from the state shown in FIG. 14E.

FIG. 14F is the view showing the lines FS2L' and FS2L when only the partial tomographic plane FSF3 is moved in the +Y direction from the state shown in FIG. 14E. In FIG. 14F, the line FS2L' before being moved is indicated by a chain double-dashed line, whereas the line FS2L' after being moved is indicated by a broken line. As shown in FIG. 14F, even in a case where only the partial tomographic plane FSF3 is moved in the +Y direction, the specific position F2P is the vertex of the isosceles triangle TR1 having, as the base, the line segment BS1 connecting the specific positions F1M and F3M, and the length of the line segment PP1 is kept the same as that of FIG. 14E. As shown in FIG. 14F, even in a case where only the partial tomographic plane FSF3 is moved, the line FS2L' indicated by a broken line is subjected to the correction in which the corner portions thereof, at which the line FS2L' changes its shape steeply, are rounded, to thereby generate the line FS2L indicated by a solid line.

Although the length of the line segment PP1 is determined based on the shape of a dentition having a normal shape, it is conceivable that the length of the line segment PP1 can be changed through designation by the operator. The shape of the isosceles triangle TR1 can be appropriately changed. For example, the isosceles triangle TR1 may be a scalene triangle in which the position of the specific position F2P with respect to the base BS1 is leaned to the lower jaw side at a certain rate.

In the modifications described with reference to FIGS. 14A to 14F, among the partial tomographic planes FSF1 to FSF3 used in setting of the tomographic plane FS2 shown in FIGS. 13A to 13C, the partial tomographic plane FSF2 is omitted. Alternatively, it is conceivable to omit any one of the other partial tomographic planes FSF1 and FSF3.

Figure 15A:
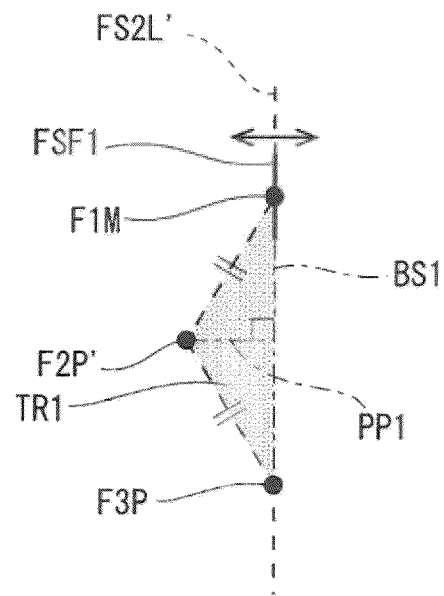
FIG. 15A is a view showing a state of setting the position of the tomographic plane FS2 with the use of only the partial tomographic plane FSF1.
Figure 15B:
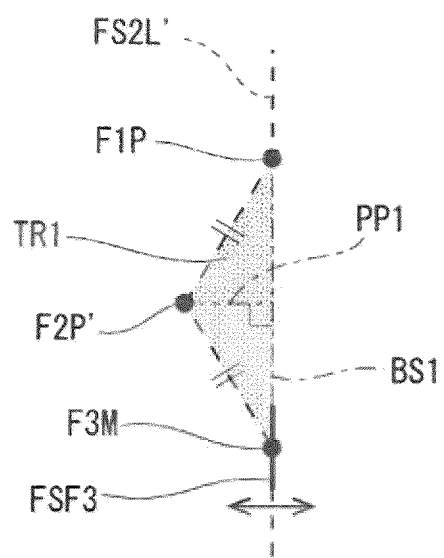
FIG. 15B is a view showing a state of setting the position of the tomographic plane FS2 with the use of only the partial tomographic plane FSF3.

FIG. 15A is a view showing a state of setting the position of the tomographic plane FS2 with the use of only the partial tomographic plane FSF1. FIG. 15B is a view showing a state of setting the position of the tomographic plane FS2 with the use of only the partial tomographic plane FSF3.

In the example shown in FIG. 15A, the line FSF2L' is determined by the specific position F1M of the partial tomographic plane FSF1 shown in FIG. 14C, a specific position F2P' located at the same position as the specific position F2P shown in FIG. 14C, and a specific position F3P located at the same position as the specific position F3M of the partial tomographic plane FSF3 shown in FIG. 14C. Specifically, the line FS2L' is formed of the straight line drawn from the upper portion of the upper jaw to the specific position F1M, the line segment connecting the specific positions F1M and F2P', the line segment connecting the specific positions F2P' and F3P, and the straight line drawn from the specific position F3P toward the lower portion of the lower jaw.

The specific position F2P' is the vertex of an isosceles triangle TR1 having, as the base, a ling segment BS1 connecting the specific positions F1M and F3P. The length of the line segment PP1 is kept the same during the operation of moving a tomographic plane, and the length of the line segment PP1 can be appropriately adjusted by the operator. Alternatively, the positions of the specific positions F1M, F2P', and F3P are not necessarily required to be vertices of an isosceles triangle.

In the example shown in FIG. 15B, the line FS2L' is determined by the specific position F1P located at the same position as the specific position F1M of the partial tomographic plane FSF1 shown in FIG. 14, the specific position F2P' located at the same position as the specific position F2P shown in FIG. 14, and the specific position F3M of the partial tomographic plane FSF3. The shape of the standard tomographic plane FS1 is not limited to the shape described above. For example, the standard tomographic plane FS1 itself may be a tomographic plane FS2' (not shown) having a shape to project toward the (−Y) direction as closer to the center portion in the Z-axis direction, similarly to the tomographic plane FS2 of FIG. 7B after the above-mentioned position adjustment. Setting may be made such that any of the above-mention partial area frames F1 to F3 is displayed on the image for position setting in a superimposed manner, and the position of the tomographic plane at one location is adjusted, to thereby allow the entire tomographic plane FS2' to move back and forth in the depth direction. Alternatively, setting may be made such that all of the above-mentioned partial area frames F1 to F3 or part of a plurality thereof are displayed in a superimposed manner and that the adjustment is partially made back and forth in the depth direction for each height in the Z-axis direction. This is effective in a case where the number of partial area frames is less than three as described above.

The partial tomographic planes FSF1, FSF2, and FSF3 described above may be each set on a tomographic plane (as to the XY coordinates, which pass through the same coordinates even if the heights differ from each other in the Z-axis direction) whose plane extends in the vertical direction within the range of each partial area. Alternatively, the partial tomographic planes FSF1, FSF2, and FSF3 may be each set on a tomographic plane extending toward the direction of its inclination, which is obtained by partially adopting, for each of different heights, a part of the tomographic plane having a shape to project toward the (−Y) direction as closer to the middle portion in the Z-axis direction including at least the median portion, such as the above-mentioned tomographic plane FS2 after position adjustment.

<Manner of Position Setting Using Only Partial Panoramic Tomographic Images>

In the example of setting the position of the tomographic plane FS2 that is described with reference to FIGS. 4 and 5, the image for position designation PA11 is displayed on the display screen W1. Alternatively, it is conceivable to display the partial panoramic tomographic images PF1, PF2, and PF3 on the display screen W1 as the images for position setting and omit the display of the image for position designation PA11. In this case, the partial panoramic tomographic images PF1, PF2, and PF3, that is, median-portion X-ray images serve as the images for position setting. Still alternatively, the example of position setting of the tomographic plane FS2 described with reference to FIGS. 14A to 14F may be modified, and the display of the image for position designation PA11 may be omitted, so that only the partial panoramic tomographic images PF1 and PF3 serve as the images for position setting.

<Manner of Position Setting Using Plain X-Ray Projection Image>

The median portion (portion including the front teeth of the upper jaw and the lower jaw) that is imaged in the image for position designation PA11 or the partial panoramic tomographic images PF1 and PF3 is the human head viewed from the front. Alternatively, it is also possible to generate the median-portion X-ray image in which the median portion is imaged, with the use of a plain X-ray projection image obtained by irradiating the head with X-rays from the side. The position of the tomographic plane FS2 may be set through display of the median-portion X-ray image on the display screen W1.

In this case, it suffices that as shown in, for example, FIG. 4, the partial tomographic planes FSF1 to FSF3 are displayed on the plain X-ray projection image (image for position setting) in which the front teeth FT1 of the upper jaw and the front teeth FT2 of the lower jaw are imaged so that the partial tomographic planes FSF1 to FSF3 are moved through the input of a predetermined operation by the operator. Needless to say, the position of the tomographic plane FS2 may be set with the use of only part of the partial tomographic planes FSF1 to FSF3, as described with reference to, for example, FIG. 14A or FIG. 15A.

In the example shown in FIG. 5 in which the partial panoramic tomographic images PF1, PF2, and PF3 are displayed, images that constitute an image for position setting are generated with the use of the image data obtained in panoramic X-ray tomography. Accordingly, it is not required to separately perform X-ray imaging, whereby an amount of X-ray exposure of the object can be suppressed. When the plain X-ray projection image (median-portion X-ray image) in which the median portion is used as an image for position setting, an amount of X-ray irradiation can be suppressed owing to the plain X-ray projection image.

<1.3 Flows of Panoramic X-Ray Tomography and Panoramic Tomography X-Ray Image Generation>

Figure 8:
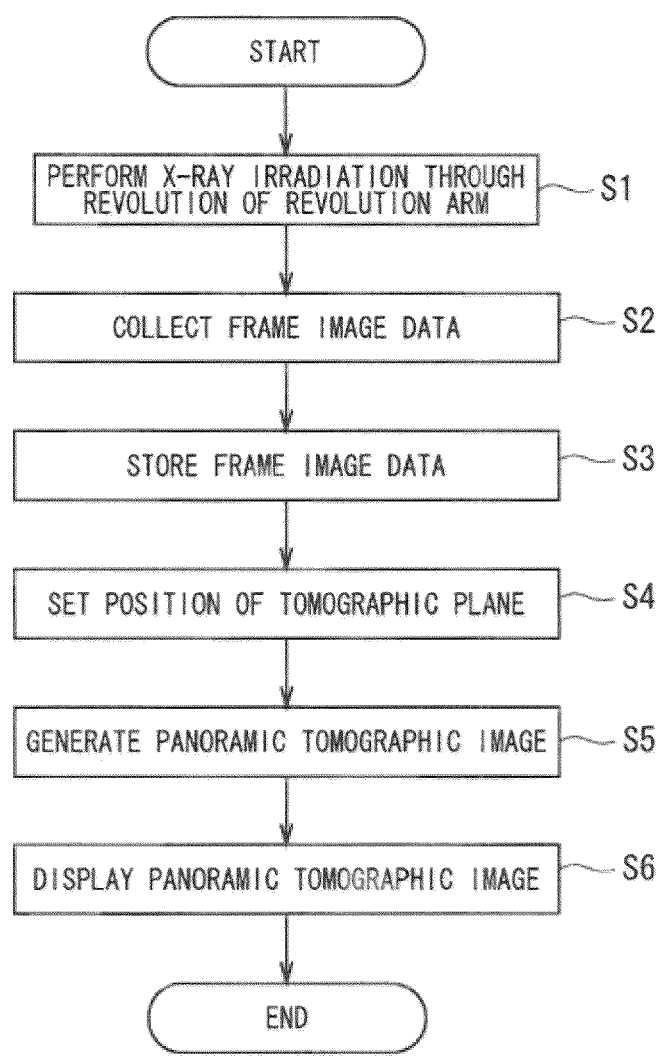
FIG. 8 is a flowchart of panoramic X-ray tomography.

FIG. 8 is a flowchart of panoramic X-ray tomography. As described above, in a case of performing panoramic X-ray tomography, X-ray irradiation is performed on the object M1 when the revolution arm 30 revolves (Step S1). Then, frame image data is obtained (Step S2), and the frame image data is stored in the storage part 802 (Step S3).

When the frame image data is obtained, position setting of the tomographic plane FS2 for generating a panoramic tomographic image is performed (Step S4). Further, an additional process is performed along the set tomographic plane FS2, whereby a panoramic tomographic image is generated (Step S5). Then, the generated panoramic tomographic image is displayed on the display part 81 (Step S6).

Figure 9:
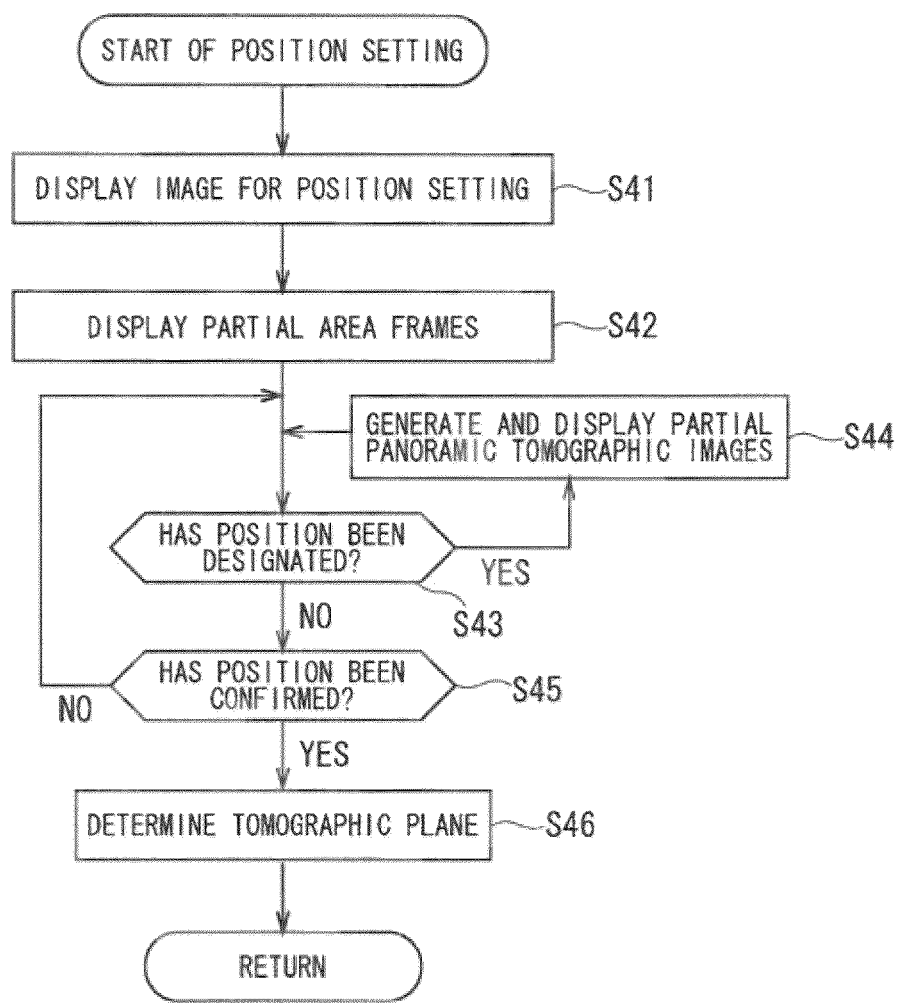
FIG. 9 is a detailed flowchart regarding position setting (Step S4) of a tomographic plane.

FIG. 9 is a detailed flowchart regarding the position setting (Step S4) of the tomographic plane FS2. The position setting of the tomographic plane FS2 is advanced in a manner described with reference to FIG. 4 to FIG. 6. More specifically, as shown in FIG. 4, the standard panoramic tomographic image P1 regarding the standard tomographic plane FS1 is generated, and the standard panoramic tomographic image P1 is displayed on the display part 81 as the image for position designation PA11 (Step S41). Then, the partial area frames F1, F2, and F3 are displayed on the image for position designation PA11 (Step S42). This image display is performed under the control of the position setting part 801a.

The position setting part 801*a* judges whether or not a position has been designated for any of the partial tomographic planes FSF1 to FSF3 corresponding to the partial area frames F1 to F3 (Step S43). The position setting part 801*a* monitors an input of the operation via the operation part 82, whereby the above-mentioned judgement is performed based on the presence or absence of the input of the operation for designating a position. In a case where a position has been designated (Yes in Step S43), the partial panoramic tomographic images PF1 to PF3 regarding the partial tomographic planes FSF1 to FSF3 at the designated position are generated by the image information processing part 801*b*. Then, the generated partial panoramic tomographic images PF1 to PF3 are displayed in the partial area frames F1 to F3 corresponding thereto (Step S44).

In a case where a position has not been designated in Step S43 (No in Step S43), the position setting part 801*a* judges whether to confirm the position of the tomographic plane FS2 (Step S44). The judgement of Step S45 is performed based on whether or not an input of the operation regarding the confirmation has been made. In a case where the position of the tomographic plane FS2 has been confirmed (Yes in Step S45), the tomographic plane FS2 is finally determined (Step S46). As described with reference to FIG. 6, in Step S46, the tomographic plane FS2 is set so as to pass through the positions Pos1 to Pos3 of the partial tomographic planes FSF1 to FSF3. In a case where the position of the tomographic plane FS2 has not been confirmed (No in Step S45), the position setting part 801*a* returns to Step S43, and receives the input of the operation of designating positions in the depth direction of the partial tomographic planes FSF1 to FSF3.

Figure 10:
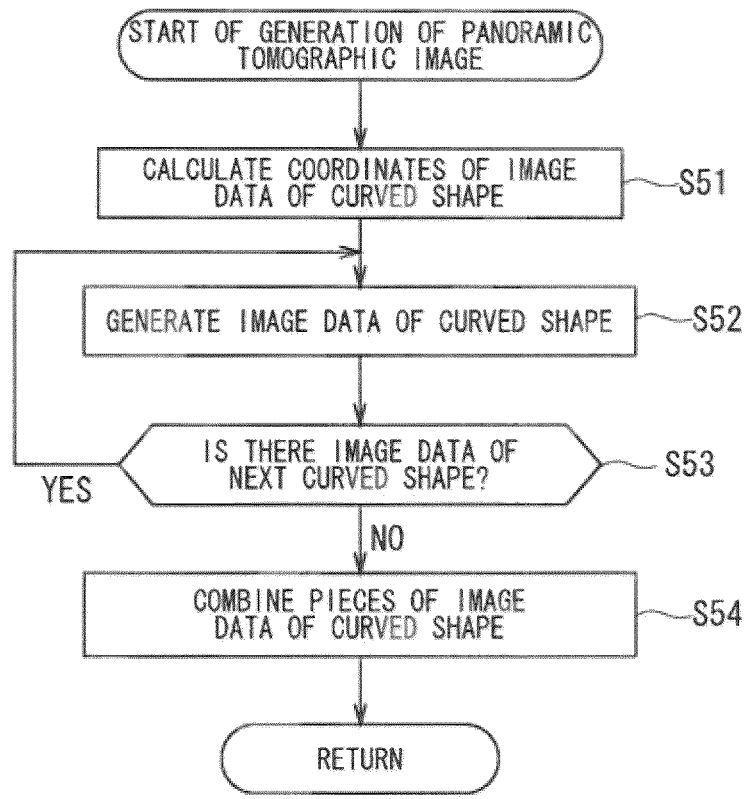
FIG. 10 is a detailed flowchart of generation of a panoramic tomographic image (Step S5)

FIG. 10 is a detailed flowchart of the generation of a panoramic tomographic image (Step S5). The panoramic tomographic image is generated in a manner described with reference to FIGS. 7A and 7B. In other words, when the tomographic plane FS2 is determined in Step S46, XY coordinates of the image data on the curved shape of the dental arch that is matched with the shape of the tomographic plane FS2 are calculated for each amount of one pixel in height regarding the Z-axis direction (Step S51).

In accordance with the calculated coordinates, pieces of image data on a curved shape of a dental arch, which are matched with the shape of the tomographic plane FS2, are generated for each amount of one pixel in height in the Z-axis direction through an addition process (Step S52). When the image data on a curved shape of one dental arch is generated, it is judged whether or not image data on a curved shape of a dental arch at the next height needs to be generated (Step S53). In a case where the next image data needs to be generated (Yes in Step S53), the routine returns to Step S52, and image data on a curved shape of the next dental arch is generated.

In a case where image data on a curved shape of a dental arch is generated for all of the heights set in the Z-axis direction of the tomographic plane FS2 (No in Step S53), the generated all pieces of image data on the curved shapes of the dental arch are combined through binding for the Z-axis direction (Step S54). As a result, a panoramic tomographic image regarding the tomographic plane FS2 is generated.

According to this preferred embodiment, the position of the tomographic plane FS2 can be set regarding the depth direction for the median line L1. As a result, the tomographic plane FS2 can be set in consideration of the shapes of the front teeth FT1 and FT2, which enables to obtain a clear panoramic tomographic image.

Furthermore, the partial area frames F1 to F3 for designating the position regarding the depth direction are set, and the positions in the depth direction of the partial tomographic planes FSF1 to FSF3 corresponding to the partial area frames F1 to F3 are changed, whereby the partial panoramic tomographic images PF1 to PF3 at the changed positions are generated and displayed in the partial area frames F1 to F3, respectively. Therefore, the partial panoramic tomographic images PF1 to PF3 are updated in real time, which makes it easy to obtain an optimum position.

In addition, the partial area frames F1 to F3 can be matched with the areas including the tooth root portions RT1 and RT2 or tooth crown portions CT1 and CT2 of the front teeth FT1 and FT2. For this reason, the optimum positions in the depth direction of the partial tomographic planes FSF1 to FSF3 can be specified by using, as indicators, the shapes of the tooth root portions RT1 and RT2 (particularly, root apex portions RTe1 and RTe2 and a portion in the vicinity thereof) or the tooth crown portions CT1 and CT2 (particularly, tip portions CTe1 and CTe2 and a portion in the vicinity thereof). The tomographic plane FS2 is set so as to pass through the positions Pos1 to Pos3 in the depth direction of the partial tomographic planes FSF1 to FSF3 matched with the optimum position in this manner. This enables to set the tomographic plane FS2 corresponding to the actual shape of the dentition 90. Therefore, the tomographic plane FSF2 faithful to the shape of the dentition 90 can be set, which enables to generate a panoramic tomographic image suitable for diagnosis.

2. Modifications

While the preferred embodiment has been described above, the present invention is not limited to the one described above and can be modified in various manners.

For example, the standard panoramic tomographic image P1 is displayed as the image for position designation PA11 in the preferred embodiment. However, the image for position designation PA11 is not limited to this. For example, a cephalogram obtained by taking an image of the dentition 90 from the side through cephalic imaging may be used as the image for position designation PA11. In this case, for example, the partial tomographic planes FSF1 to FSF3 shown in the cross-section of the dentition in FIG. 4 (or FIG. 5) are displayed on the cephalogram. Then, it suffices that the partial tomographic planes FSF1 to FSF3 are moved along the depth direction to designate the positions in the depth direction thereof.

The cephalostat 43 is provided with a head fixture 431, which enables to set a reference position (not shown) based on the position of the head fixture 431 and calculate adjusted positions of the tomographic planes FSF1 to FSF3 with respect to the reference position. The cephalogram as an image for position designation is an example of images constituting an image for position setting.

Alternatively, as in the case of FIG. 5 in which the designation is made on an X-ray image of the side surface of the front tooth portion, the partial tomographic planes FSF1 to FSF3 may be designated by, for example, irradiating the head fixed to the object fixing part 421, especially, the front tooth portion from the side with an X-ray beam from the X-ray generator 13, detecting the X-ray beam by the X-ray detector 21, generating an X-ray image of the side surface of the front tooth portion, and displaying the X-ray image displayed on the display part 81 as the image for position setting. It is possible to set a reference position (not shown) based on the position of the object fixing part 421 and calculate the adjusted positions of the tomographic planes FSF1 to FSF3 with respect to the reference position. The X-ray image of the side surface of the front tooth portion as the image for position setting is an example of images constituting an image for position setting.

In the preferred embodiment above, the position of the object M1 is specified, and the movement of the X-ray generator 13 in panoramic X-ray tomography is adjusted by the adjustment part 601d based on the positional information such that the object M1 is ideally irradiated with the X-ray beam BX1. Alternatively, the position of the object M1 may be moved to a predetermined position. As a configuration for moving the object M1, the movement mechanism disclosed in, for example, Japanese Patent Application Laid-Open No. 02-140150 (1990) filed by the applicant of the present application may be appropriately adopted.

Alternatively, the position or shape of the tomographic plane FS2 may be adjusted. Such a configuration is preferred as a measure taken in a case where the dental arch is shifted from an ideal position by a movement of a patient when, for example, the patient is positioned. FIG. 11 shows a configuration example thereof.

FIG. 11 is an explanatory view for explaining the displacement adjustment or shape adjustment of the tomographic plane FS2. In the example shown in FIG. 11, the displacement adjustment or shape adjustment is performed as described below. In the description below, the front-and-back direction (Y-axis direction), the right-and-left direction (X-axis direction), and the up-and-down direction (Z-axis direction) are each set relative to the human head.

(1) The entire tomographic plane FS2 is adjusted to be displaced forward (toward a direction DFW, that is, −Y direction).

(2) The entire tomographic plane FS2 is adjusted to be displaced backward (toward a direction DRV, that is, +Y direction).

(3) The entire tomographic plane FS2 is adjusted to be displaced rightward (toward a direction DR, that is, −X direction).

(4) The entire tomographic plane FS2 is adjusted to be displaced leftward (toward a direction DL, that is, +X direction).

(5) The entire tomographic plane FS2 is adjusted to be displaced upward (toward a direction DUP, that is, +Z direction).

(6) The entire tomographic plane FS2 is adjusted to be displaced downward (toward a direction DLW, that is, −Z direction).

(7) The entire tomographic plane FS2 is adjusted to be displaced through rotation clockwise (toward a direction DRLU) about a virtual rotation axis VA1. The virtual rotation axis VA1 is set to extend immediately backward from the portion in the vicinity of the center of the front teeth.

(8) The entire tomographic plane FS2 is adjusted to be displaced through rotation counterclockwise (toward a direction DRRU) about the virtual rotation axis VA1.

(9) The entire tomographic plane FS2 is adjusted to be displaced through forward tilting to turn forward (toward a direction DRFU) about a virtual rotation axis VA2. The virtual rotation axis VA2 is set to, for example, extend toward the right and left from the portion in the vicinity of the center of the front teeth. The rotation axis VA2 may be set to another position. For example, the rotation axis VA2 may be set to penetrate the portions in the vicinity of the occlusion of the innermost right and left molars.

(10) The entire tomographic plane FS2 is adjusted to be displaced through backward tilting to turn backward (toward a direction DRBU) about the virtual rotation axis VA2.

(11) The entire tomographic plane FS2 is adjusted to be displaced through rotation rightward (toward a direction DRRT) about a virtual rotation axis VA3. The virtual axis V3 is set to, for example, extend upward and downward in the vicinity of the center of the front teeth.

(12) The entire tomographic plane FS2 is adjusted to be displaced through rotation counterclockwise (toward a direction DRLT) about the virtual rotation axis VA3.

(13) The shape is adjusted such that the right portion of the tomographic plane FS2 is widened outwardly (toward a direction DRW) about the virtual rotation axis VA3. In this shape adjustment, the curvature of the right portion of the tomographic plane FS2 may be set to appropriately change. The adjustment as described above is effective in a case where the imaged dental arch is widened more than assumed.

(14) The shape is adjusted such that the right portion of the tomographic plane FS2 is narrowed inwardly (toward a direction DRN) about the virtual axis VA3. In this shape adjustment, the curvature of the right portion of the tomographic plane FS2 may be set to appropriately change. The adjustment as described above is effective in a case where the imaged dental arch is widened less than assumed.

(15) The shape is adjusted such that the left portion of the tomographic plane FS2 is widened outwardly (toward a direction DLW) about the virtual axis VA3. In this shape adjustment, the curvature of the left portion of the tomographic plane FS2 may be set to appropriately change. When the shape is adjusted for one of the direction DRW and the direction DLW, a shape adjustment may be performed on the other direction for an amount corresponding to the adjustment amount.

(16) The shape is adjusted such that the left portion of the tomographic plane FS2 is narrowed inwardly (toward a direction DLN) about the virtual axis VA3. In this shape adjustment, the curvature of the left portion of the tomographic plane FS2 may be set to appropriately change. When the shape is adjusted for one of the direction DRN and the direction DLN, a shape adjustment may be performed on the other direction for an amount corresponding to the adjustment amount.

The configuration may be made so as to allow part of the displacement adjustment and shape adjustments (1) to (16). The displacement adjustments and shape adjustments (1) to (16) are performed on the newly set tomographic plane FS2. However, a target tomographic plane for displacement or shape adjustment is not limited to the tomographic plane FS2. For example, the displacement or shape adjustment may be performed similarly on the standard tomographic plane FS1. Desired setting of the tomographic plane FS2, which is described with reference to, for example, FIG. 5, may be performed after the displacement or shape adjustment is performed on the tomographic plane FS1.

Figure 12:
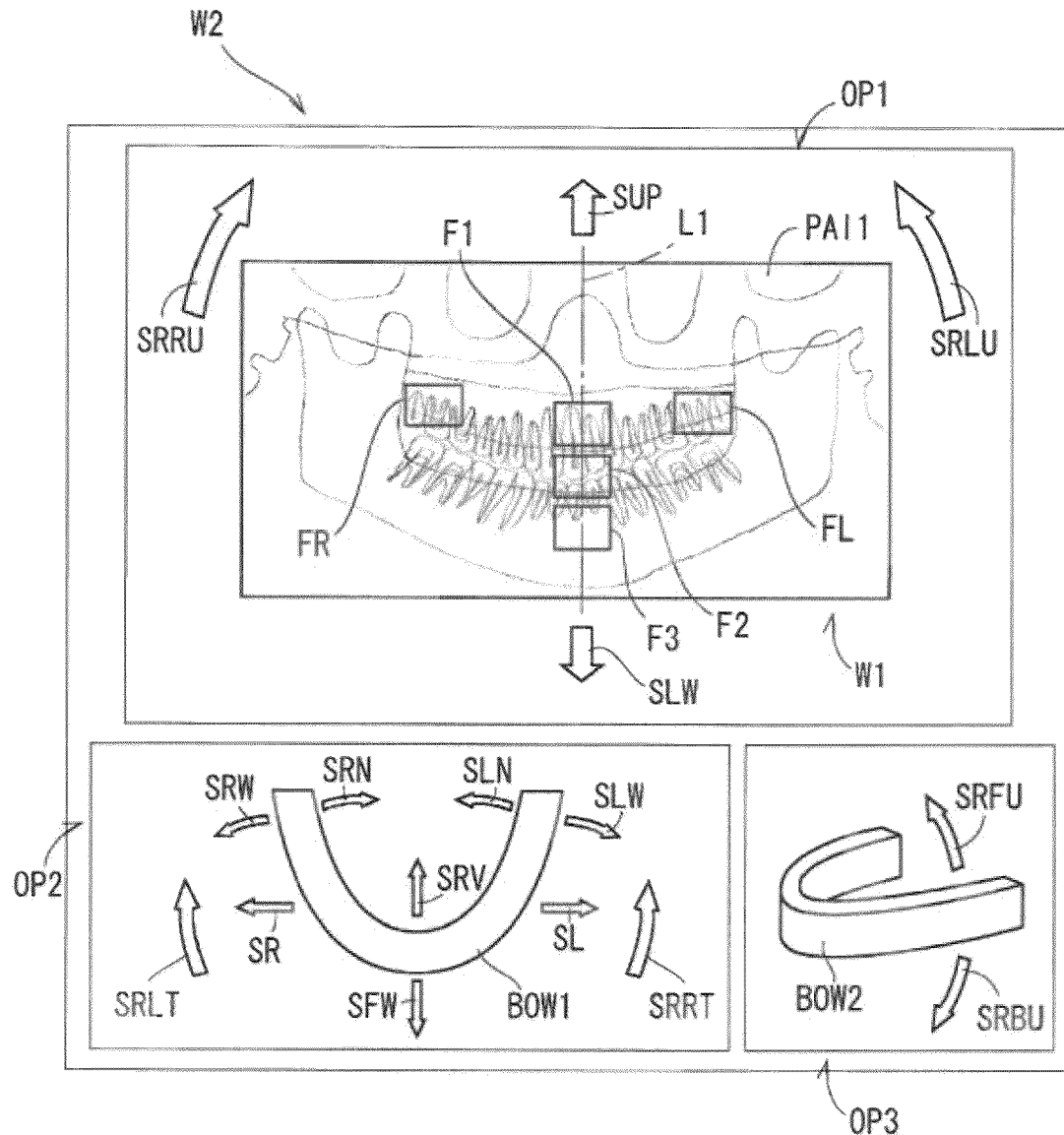
FIG. 12 is an explanatory view for explaining an example of an interface for performing the displacement adjustment or shape adjustment shown in FIG. 11.

FIG. 12 is an explanatory view for explaining an example of an interface for performing the displacement adjustment or shape adjustment shown in FIG. 11. FIG. 12 shows a display screen W2 including operation frames OP1, OP2, and OP3.

Various buttons are arranged around the display screen for position setting W1 within the operation frame OP1. In addition, various buttons are arranged around a symbol BOW1 having an arcuate shape showing a dental arch within the operation frame OP2. The symbol BOW1 schematically shows the dental arch in plane view. Various buttons are arranged behind a symbol BOW2 having an arcuate shape that shows a dental arch within the operation frame OP3. The symbol BOW2 schematically shows the dental arch when the dental arch is viewed obliquely from upper left in front thereof.

In the example shown in FIG. 12, the various buttons displayed on the display screen W2 are turned on/off with a pointer that is moved by means of a mouse or the like. The various buttons are configured such that, for example, a displacement amount in each direction is adjusted in accordance with a period of time of turning-on.

Various functions described below are assigned to the various buttons shown in FIG. 12.

(A) A button SFW is provided for instructing the displacement adjustment (the tomographic plane FS2 is displaced toward the direction DFW) of (1) above.

(B) A button SRV is provided for instructing the displacement adjustment (the tomographic plane FS2 is displaced toward the direction DRV) of (2) above.

(C) A button SR is provided for instructing the displacement adjustment (the tomographic plane FS2 is displaced toward the direction DR) of (3) above.

(D) A button SL is provided for instructing the displacement adjustment (the tomographic plane FS2 is displaced toward the direction DL) of (4) above.

(E) A button SUP is provided for instructing the displacement adjustment (the tomographic plane FS2 is displaced toward the direction DUP) of (5) above.

(F) A button SLW is provided for instructing the displacement adjustment (the tomographic plane FS2 is displaced toward the direction DLW) of (6) above.

(G) A button SRLU is provided for instructing the displacement adjustment (the tomographic plane FS2 is rotated toward the direction DRLU) of (7) above.

(H) A button SRRU is provided for instructing the displacement adjustment (the tomographic plane FS2 is rotated toward the direction DRRU) of (8) above.

(I) A button SRFU is provided for instructing the displacement adjustment (the tomographic plane FS2 is rotated toward the direction DRFU) of (9) above.

(J) A button SRBU is provided for instructing the displacement adjustment (the tomographic plane FS2 is rotated toward the direction DRBU) of (10) above.

(K) A button SRRT is provided for instructing the displacement adjustment (the tomographic plane FS2 is rotated toward the direction DRRT) of (11) above.

(L) A button SRLT is provided for instructing the displacement adjustment (the tomographic plane FS2 is rotated toward the direction DRLT) of (12) above.

(M) A button SRW is provided for instructing the shape adjustment (the tomographic plane FS2 is widened toward the direction DRW) of (13) above.

(N) A button SRN is provided for instructing the shape adjustment (the tomographic plane FS2 is narrowed toward the direction DRN) of (14) above.

(O) A button SLW is provided for instructing the shape adjustment (the tomographic plane FS2 is widened toward the direction DLW) of (15) above.

(P) A button SLN is provided for instructing the shape adjustment (the tomographic plane FS2 is narrowed toward the direction DLN) of (16) above.

The displacement and shape adjustments (1) to (16) of FIG. 11 may be performed with an appropriate adjustment amount. Alternatively, some default adjustment positions may be prepared in advance for each of (1) to (16) so that an appropriate one is selected in accordance with, for example, the number of times a mouse is clicked (setting can be made such that selections may be performed in order with one of click buttons and may be performed in inverse order with the other thereof).

The preparation of the buttons above enables to adjust the displacement or shape of the tomographic plane FS2. A partial area frame FL and a partial area frame FR may be set in the left portion and the right portion on the image for position designation PA11, respectively. As in the partial area frames F1 to F3, a partial panoramic tomographic image regarding a tomographic plane FS2 newly set through the displacement or position adjustment is displayed within the partial area frame FL or the partial area frame FR. This makes it easy to understand whether or not an adjustment amount is appropriate.

As to the partial area frames FL and FR, any of the partial area frames FL and FR is selected through a click operation of a mouse similarly to the partial area frames F1 to F3, so that a roller provided in the mouse is rotated toward any one of + and − directions of rotation for the selected partial area frame. As a result, the roller is rotated toward the other of the directions of rotation in the +Y depth direction, which may allow the position adjustment of the tomographic plane FS2 in the −Y direction. In this case, the tomographic plane FS2 undergoes an adjustment similar to, for example, the displacement adjustment (13) toward the direction DRW, the displacement adjustment (14) toward the direction DRN, the displacement adjustment (15) toward the direction DLW, or the displacement adjustment (16) toward the direction DLN described with reference to FIG. 11.

The configuration described in the preferred embodiment and modifications above can be appropriately combined unless they are not contradictory with each other.

While the invention has been shown and described in detail, the foregoing description is in all aspects illustrative and not restrictive. It is therefore understood that numerous modifications and variations can be devised without departing from the scope of the invention.

What is claimed is:

1. A panoramic tomography X-ray apparatus, comprising:
an X-ray generator for emitting X-rays;
an X-ray detector including a plurality of detection elements outputting signals corresponding to intensity of the X-rays to be incident thereon;
a revolution mechanism for causing the X-ray generator and the X-ray detector to be opposed to each other with an object including a dentition therebetween and allowing the X-ray generator and the X-ray detector to revolve about the object;
a storage part for successively storing and accumulating the signals output from the X-ray detector as an image information when the X-ray generator revolving emits the X-rays;
an image information processing part for receiving the image information from the storage part and superimposing overlapped portions of images along a tomographic plane corresponding to a dental arch to generate a panoramic tomographic image;
a display part for displaying the panoramic tomographic image generated by the image information processing part;
a position setting part for setting, in a median portion including a median line of the object, a position of the tomographic plane regarding a depth direction of the object with a use of at least one image for position setting comprising a median-portion X-ray image including the median portion; and
an operation part for receiving an input of an operation by an operator, wherein
said position setting part receives designation of a position of said tomographic plane regarding the depth direction at a partial area including said median portion with respect to said image for position setting via said operation part, and
said image information processing part causes said display part to display a new panoramic tomographic image generated by changing position of the tomographic plane corresponding to the dental arch along said depth direction in accordance with a designated position by said designation received via said operation part.

2. The panoramic tomography X-ray apparatus according to claim 1, wherein
the position setting part causes the display part to display, as an image for position designation that forms the at least one image for position setting, the panoramic tomographic image regarding the dentition, and
on the at least one image for position setting, the position setting part receives designation of a position regarding the depth direction of the tomographic plane in the median portion via the operation part and allows a display of a tomographic image of the partial area at the designated position received, as the median-portion X-ray image, on the image for position designation in a superimposed manner.

3. The panoramic tomography X-ray apparatus according to claim 2, wherein the position setting part allows a display of, for the partial area including the median portion, a panoramic tomographic image of a partial tomographic plane at the designated position as the median-portion X-ray image on the image for position designation in the superimposed manner.

4. The panoramic tomography X-ray apparatus according to claim 3, wherein a position of the partial area is changeable in a direction orthogonal to the depth direction by the input of the operation via the operation part on the image for position designation.

5. The panoramic tomography X-ray apparatus according to claim 2, wherein the position setting part receives the designation of the position regarding the depth direction for an upper jaw or a lower jaw in the median portion.

6. The panoramic tomography X-ray apparatus according to claim 2, wherein the position setting part receives the designation of the position regarding the depth direction for an area including a tooth root portion of at least one tooth located in the median portion.

7. The panoramic tomography X-ray apparatus according to claim 2, wherein the position setting part receives the designation of the position regarding the depth direction for two areas including a tooth root portion of at least one tooth located in the median portion and a tooth crown portion of the at least one tooth.

8. The panoramic tomography X-ray apparatus according to claim 2, wherein the position setting part receives the designation of the position regarding the depth direction for three areas including a tooth root portion of at least one tooth of an upper jaw, a tooth root portion of at least one tooth of a lower jaw, and occlusion portions of these teeth.

9. The panoramic tomography X-ray apparatus according to claim 1, wherein the position setting part sets the position of the tomographic plane such that the position of the tomographic plane changes along the median line in a non-linear manner regarding the depth direction of the object.

10. The panoramic tomography X-ray apparatus according to claim 1, wherein the position setting part sets the position of the tomographic plane such that the position of the tomographic plane changes along the median line L1 into a beak shape in the depth direction of the object.

11. The panoramic tomography X-ray apparatus according to claim 1, wherein the tomographic plane has a curved plane along the dental arch.

12. The panoramic tomography X-ray apparatus according to claim 1, further comprising:
a position detection part for detecting a position of the object; and
an adjustment part for adjusting a positional relationship among the object, the X-ray generator, and the X-ray detector based on detection results by the position setting part.

13. An image processing device, comprising:
a storage part for storing, when an X-ray generator emits X-rays while the X-ray generator and an X-ray detector are caused to revolve about an object including a dentition in a state of being opposed to each other with the object therebetween, signals output from the X-ray detector in accordance with intensity of the X-rays as image information when the X-ray generator being revolved by a revolution mechanism emits the X-rays;
an image information processing part for retrieving the image information from the storage part and performing a process of superimposing overlapped portions of images along a tomographic plane corresponding to a dental arch to generate a panoramic tomography image;
a display part for displaying the panoramic tomographic image generated by the image information processing part;
a position setting part for setting, in a median portion including a median line of the object, a position of the tomographic plane regarding a depth direction of the object with a use of at least one image for position setting comprising a median-portion X-ray image including the median portion; and
an operation part for receiving an input of an operation by an operator, wherein
said position setting part receives designation of a position of said tomographic plane regarding the depth direction at a partial area including said median portion with respect to said image for position setting via said operation part, and
said image information processing part causes said display part to display a new panoramic tomographic image generated by changing position of the tomographic plane corresponding to the dental arch along said depth direction in accordance with a designated position by said designation received via said operation part.

14. The image processing device according to claim 13, wherein
the position setting part causes the display part to display, as an image for position designation that forms the at least one image for position setting, the panoramic tomographic image regarding the dentition, and
on the at least one image for position setting, the position setting part receives designation of a position regarding the depth direction of the tomographic plane in the median portion via the operation part and displays a tomographic image of the partial area at the designated position received as the median-portion X-ray image on the image for position designation in a superimposed manner.

15. The panoramic tomography X-ray apparatus according to claim 1, wherein
said position setting part receives the designation of the position regarding the depth direction of said tomographic plane for each of different height positions of said dentition, and
said image information processing part changes the position of the tomographic plane corresponding to the dental arch along said depth direction in accordance with said designated position for each of said different height positions.

16. The panoramic tomography X-ray apparatus according to claim 1, wherein the tomographic plane corresponding to the dental arch contains a portion extending toward the direction of its inclination.

17. The panoramic tomography X-ray apparatus according to claim 1, wherein the median-portion X-ray image is a plain X-ray projection image obtained by irradiating the dentition with X-rays from the side.

18. A panoramic tomography X-ray apparatus, comprising:
   an X-ray generator for emitting X-rays;
   an X-ray detector including a plurality of detection elements outputting signals corresponding to intensity of the X-rays to be incident thereon;
   a revolution mechanism for causing the X-ray generator and the X-ray detector to be opposed to each other with an object including a dentition therebetween and allowing the X-ray generator and the X-ray detector to revolve about the object;
   a storage part for successively storing and accumulating the signals output from the X-ray detector as an image information when the X-ray generator revolving emits the X-rays;
   an image information processing part for receiving the image information from the storage part and superimposing overlapped portions of images along a tomographic plane corresponding to a dental arch to generate a panoramic tomographic image;
   a display part for displaying the panoramic tomographic image generated by the image information processing part;
   a position setting part for setting, in a median portion including a median line of the object, a position of the tomographic plane regarding a depth direction corresponding to a front-back direction of the object with a use of at least one image for position setting comprising a median-portion X-ray image including the median portion; and
   an operation part for receiving an input of an operation by an operator, wherein
   said image for position setting includes an image displaying an X-ray image of a partial area including said median portion on an image for position designation formed of an X-ray image of the entire dentition in a superimposed manner,
   one or more of the X-ray image of said partial area are arranged in a longitudinal direction along said median line in said median portion in the X-ray image of said entire dentition, the X-ray image of said partial area being a tomographic image of only said partial area along the tomographic plane of said panoramic tomographic image,
   the position designation regarding said depth direction is performed by said operation part receiving operation of adjusting the position of each tomographic plane of the tomographic image of only said partial area to move individually in said depth direction, and
   said image information processing part causes said display part to display a new panoramic tomographic image generated by changing position of the tomographic plane corresponding to the dental arch along a designated position by said position designation received via said operation part.

19. The panoramic tomography X-ray apparatus according to claim 18, wherein two or three of the X-ray images of said partial area are arranged in the longitudinal direction along said median line.

20. The panoramic tomography X-ray apparatus according to claim 18, wherein the position of said partial area is configured to move at least in said longitudinal direction.

21. An image processing device, comprising:
   a storage part for storing, when an X-ray generator emits X-rays while the X-ray generator and an X-ray detector are caused to revolve about an object including a dentition in a state of being opposed to each other with the object therebetween, signals output from the X-ray detector in accordance with intensity of the X-rays as image information when the X-ray generator being revolved by a revolution mechanism emits the X-rays;
   an image information processing part for retrieving the image information from the storage part and performing a process of superimposing overlapped portions of images along a tomographic plane corresponding to a dental arch to generate a panoramic tomography image;
   a display part for displaying the panoramic tomographic image generated by the image information processing part;
   a position setting part for setting, in a median portion including a median line of the object, a position of the tomographic plane regarding a depth direction corresponding to a front-and-back direction of the object with a use of at least one image for position setting comprising a median-portion X-ray image including the median portion; and
   an operation part for receiving an input of an operation by an operator, wherein
   said image for position setting includes an image displaying an X-ray image of a partial area including said median portion on an image for position designation formed of an X-ray image of the entire dentition in a superimposed manner,
   one or more of the X-ray image of said partial area are arranged in a longitudinal direction along said median line in said median portion in the X-ray image of said entire dentition, the X-ray image of said partial area being a tomographic image of only said partial area along the tomographic plane of said panoramic tomographic image,
   the position designation regarding said depth direction is performed by said operation part receiving operation of adjusting the position of each tomographic plane of the tomographic image of only said partial area to move individually in said depth direction, and
   said image information processing part causes said display part to display a new panoramic tomographic image generated by changing position of the tomographic plane corresponding to the dental arch along a designated position received via said operation part.

22. The image processing device according to claim 21, wherein two or three of the X-ray images of said partial area are arranged in the longitudinal direction along said median line.

23. The image processing device according to claim 21, wherein the position of said partial area is configured to move at least in said longitudinal direction.

* * * * *